US012667942B2

(12) United States Patent
Nilsson

(10) Patent No.: US 12,667,942 B2
(45) Date of Patent: Jun. 30, 2026

(54) COUNTER-TORQUE DRIVER TOOL

(71) Applicant: C-Torq, LLC, Moreland Hills, OH (US)

(72) Inventor: Carl Michael Nilsson, Moreland Hills, OH (US)

(73) Assignee: c-Torq, LLC, Moreland Hills, OH (US)

( * ) Notice: Subject to any disclaimer, the term of this patent is extended or adjusted under 35 U.S.C. 154(b) by 385 days.

(21) Appl. No.: 17/898,900

(22) Filed: Aug. 30, 2022

(65) Prior Publication Data

US 2023/0073756 A1     Mar. 9, 2023

Related U.S. Application Data

(60) Provisional application No. 63/264,117, filed on Nov. 16, 2021, provisional application No. 63/238,522, filed on Aug. 30, 2021.

(51) Int. Cl.
B25B 13/48       (2006.01)
A61B 17/88       (2006.01)
(Continued)

(52) U.S. Cl.
CPC .......... B25B 13/48 (2013.01); A61B 17/8875 (2013.01); B25B 13/467 (2013.01);
(Continued)

(58) Field of Classification Search
CPC ..... B25B 13/48; B25B 13/488; B25B 13/467; B25B 15/00; B25B 15/02; B25B 15/04;
(Continued)

(56) References Cited

U.S. PATENT DOCUMENTS 2,928,302 A     3/1960  Arthur et al.
3,294,183 A     12/1966  Riley, Jr. et al.
(Continued)

FOREIGN PATENT DOCUMENTS

EP        1614506 A1     1/2006
WO     2014014707 A1     1/2014
WO     2018175877 A1     9/2018

OTHER PUBLICATIONS

The International Search Report and the Written Opinion of the International Searching Authority of the corresponding PCT application, PCT/US2022/041998, dated Nov. 22, 2022, 10 pages.
(Continued)

*Primary Examiner* — Robert J Scruggs
(74) *Attorney, Agent, or Firm* — Tucker Ellis LLP; Michael G. Craig; Bennett E. Kuhar

(57)                    ABSTRACT

One or more techniques and/or systems are disclosed for a tool driver device that can apply counter-torque to the device while applying torque to a target component that is engaging a target base. The example device can be operated by one hand to actuate a power input component that provides the desired torque, while providing counter-torque to offset rotation of the device. A selectably engaged counter-torque component is selected to complement the target base, to operably hold it in place during use. A power input provides power to apply rotational force to drive a selectably coupled tool, which has been selected to complement the target component engaged with a target base. The counter-torque component is operably engaged with the base, which applies counter-torque to the torque provided by the target component.

18 Claims, 35 Drawing Sheets

(51) Int. Cl.

| | |
|---|---|
| *B25B 13/46* | (2006.01) |
| *B25B 21/00* | (2006.01) |
| *B25B 23/14* | (2006.01) |
| *A61B 17/00* | (2006.01) |

(52) U.S. Cl.

CPC .......... *B25B 21/002* (2013.01); *B25B 23/141* (2013.01); *A61B 2017/00398* (2013.01); *A61B 2017/00407* (2013.01)

(58) Field of Classification Search

CPC ....... B25B 17/00; B25B 17/02; B25B 21/002; B25B 21/004; B25B 21/007; B25B 21/008; B25B 23/0057; B25B 23/0064; B25B 23/0071; B25B 23/0078; B25B 23/0085; B25B 23/14; B25B 23/141; B25B 23/142; B25B 23/1422; B25B 23/147; A61B 17/8875; A61B 2017/00398; A61B 2017/00407; A61B 17/7074; A61B 17/7032; A61B 17/7086; A61B 17/7091

See application file for complete search history.

(56) References Cited

U.S. PATENT DOCUMENTS

| | | | |
|---|---|---|---|
| 3,324,747 | A | 6/1967 | Able |
| 4,739,838 | A | 4/1988 | Marks |
| D303,204 | S | 9/1989 | Marks |
| 5,108,238 | A | 4/1992 | Ewing |
| 5,238,461 | A * | 8/1993 | Gotman ................ B25B 13/488 |
| | | | 475/248 |
| 5,354,246 | A | 10/1994 | Gotman |
| 5,540,629 | A | 7/1996 | Gotman |
| 5,582,079 | A | 12/1996 | Matsumura et al. |
| 5,964,128 | A | 10/1999 | Kaneyama et al. |
| 6,058,810 | A | 5/2000 | Junkers |
| 6,487,940 | B2 | 12/2002 | Hart et al. |
| 7,204,667 | B2 | 4/2007 | Uno et al. |
| 7,641,579 | B2 | 1/2010 | Junkers |
| 7,735,397 | B2 | 6/2010 | Junkers |
| 7,794,355 | B2 | 9/2010 | Pusateri |
| 7,987,745 | B2 * | 8/2011 | Gauthier ................ B25B 17/00 |
| | | | 81/58.3 |
| 8,220,365 | B2 | 7/2012 | Yang |
| 8,225,698 | B2 | 7/2012 | Yang |
| 8,225,699 | B2 | 7/2012 | Yang |
| 8,590,429 | B2 | 11/2013 | Goss et al. |
| 8,978,523 | B2 | 3/2015 | Stanfield et al. |
| 9,017,333 | B2 | 4/2015 | Beale et al. |
| 9,532,814 | B2 | 1/2017 | Harper |
| 9,744,654 | B2 * | 8/2017 | Bootwala ........... A61B 17/7091 |
| 9,918,755 | B2 | 3/2018 | Bootwala et al. |
| 10,493,603 | B2 * | 12/2019 | Dekam ................... B25B 17/00 |
| 10,562,159 | B2 | 2/2020 | Bassett et al. |
| 10,772,663 | B2 | 9/2020 | Harper |
| 11,148,260 | B2 | 10/2021 | Larson |
| 2014/0130640 | A1 * | 5/2014 | Marks ................... B25B 13/463 |
| | | | 81/57.39 |
| 2014/0276896 | A1 * | 9/2014 | Harper ............... A61B 17/8872 |
| | | | 606/104 |
| 2014/0277203 | A1 * | 9/2014 | Atoulikian .............. B25B 17/02 |
| | | | 606/86 A |
| 2016/0374735 | A1 * | 12/2016 | Bootwala ........... A61B 17/7091 |
| | | | 606/86 A |
| 2017/0266771 | A1 | 9/2017 | Inowaki |
| 2018/0036046 | A1 * | 2/2018 | Yim ................... A61B 17/7091 |
| 2019/0120275 | A1 | 4/2019 | Junkers et al. |

OTHER PUBLICATIONS

Partial European Search Report for related European application No. 24183092.6, dated Apr. 22, 2025, 14 pages.

* cited by examiner

COUNTER-TORQUE DRIVER TOOL

CROSS-REFERENCE TO RELATED APPLICATIONS

This application claims priority to U.S. provisional Ser. No. 63/264,117, entitled COUNTER-TORQUE FASTENER DRIVER, filed on Nov. 16, 2021, and claims priority to U.S. provisional Ser. No. 63/238,522, entitled COUNTER-TORQUE FASTENER DRIVER, filed on Aug. 30, 2021, all of which are incorporated herein by reference.

BACKGROUND

A driver-type tool can be used to drive a fastener into (or out of) a target component. When driving the fastener into the target component torque is applied to the fastener by the driver, and counter-torque can be applied to the driver by a user (e.g., manually). When torque is applied to the fastener counter-torque is applied to the driver and/or the target component in order to allow the fastener to drive into the component (e.g., due to friction, etc.), otherwise either the target component will rotate with the fastener, or the driver will rotate in the intended rotational direction of the shaft. Typically, the needed counter-torque must be applied by the user with a separate device and/or some type of external stabilizing frame.

SUMMARY

This Summary is provided to introduce a selection of concepts in a simplified form that are further described below in the Detailed Description. This Summary is not intended to identify key factors or essential features of the claimed subject matter, nor is it intended to be used to limit the scope of the claimed subject matter.

One or more techniques and systems are described herein for a tool driver device that applies torque to a target tool, such as one that is configured to engage a target component, while applying counter-torque to a target base that is engaged with the target component. That is, for example, the exemplary device can apply torque to a tool, such as a screwdriver head or socket head, etc., to drive a complementary target component, such as a screw, nut or bolt, etc. In this example, counter-torque can be applied to target base with which the target component is engaged, such as a surface, a frame, nut or bolt, etc., to counter-rotation of the target base. In this way, for example, the counter-rotation may be transferred to the device itself, making for easier operation. In some implementations, the exemplary device can provide for a one-hand operation, utilizing a type of trigger that, when activated, applies a desired amount of torque at the target tool end, while mitigating counter-rotation of the device in the user's hand.

In one implementation, the exemplary device applies torque to rotate a target tool engaging a complementary target component and applies counter torque to stabilize the device with regard to a target base engaged with the target component. In this implementation, the exemplary device comprises a housing that is configured to be operably held by an operator. Further, the exemplary device comprises a rotating shaft that rotates relative to the housing to operably provide torque to the target tool. A power input operably provides power to the rotating shaft. Additionally, a counter-torque component comprises a body that is configured to selectably, fixedly engage with the target base to apply counter-torque to the target base.

To the accomplishment of the foregoing and related ends, the following description and annexed drawings set forth certain illustrative aspects and implementations. These are indicative of but a few of the various ways in which one or more aspects may be employed. Other aspects, advantages and novel features of the disclosure will become apparent from the following detailed description when considered in conjunction with the annexed drawings.

DETAILED DESCRIPTION

Figures 1A, 1B, 1C:
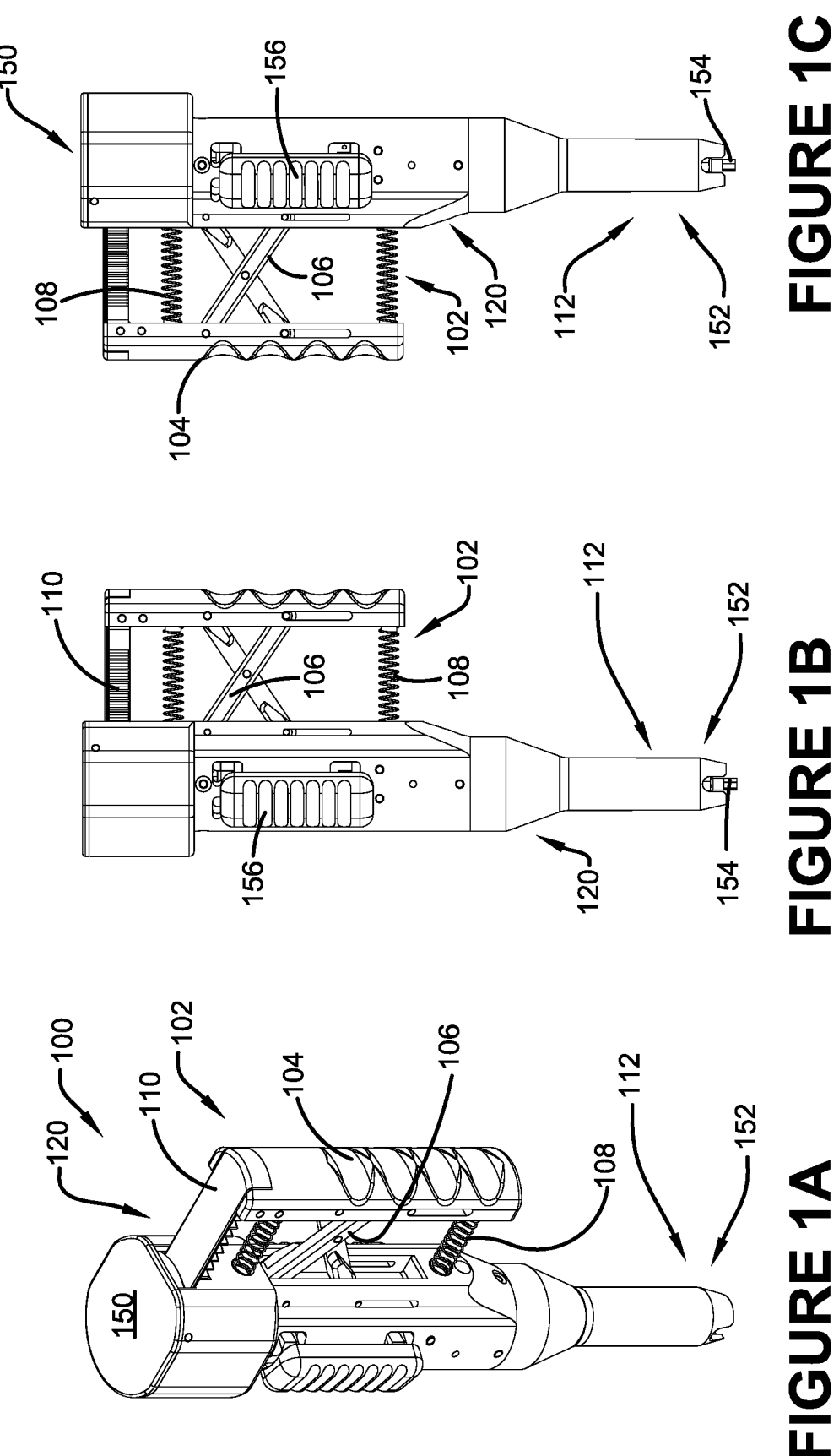
FIGS. 1A-1G are component diagram illustrating one example implementation of a fastener driving device that can be operated one-handed and can provide torque and counter-torque.
Figures 1D, 1E, 1F, 1G:
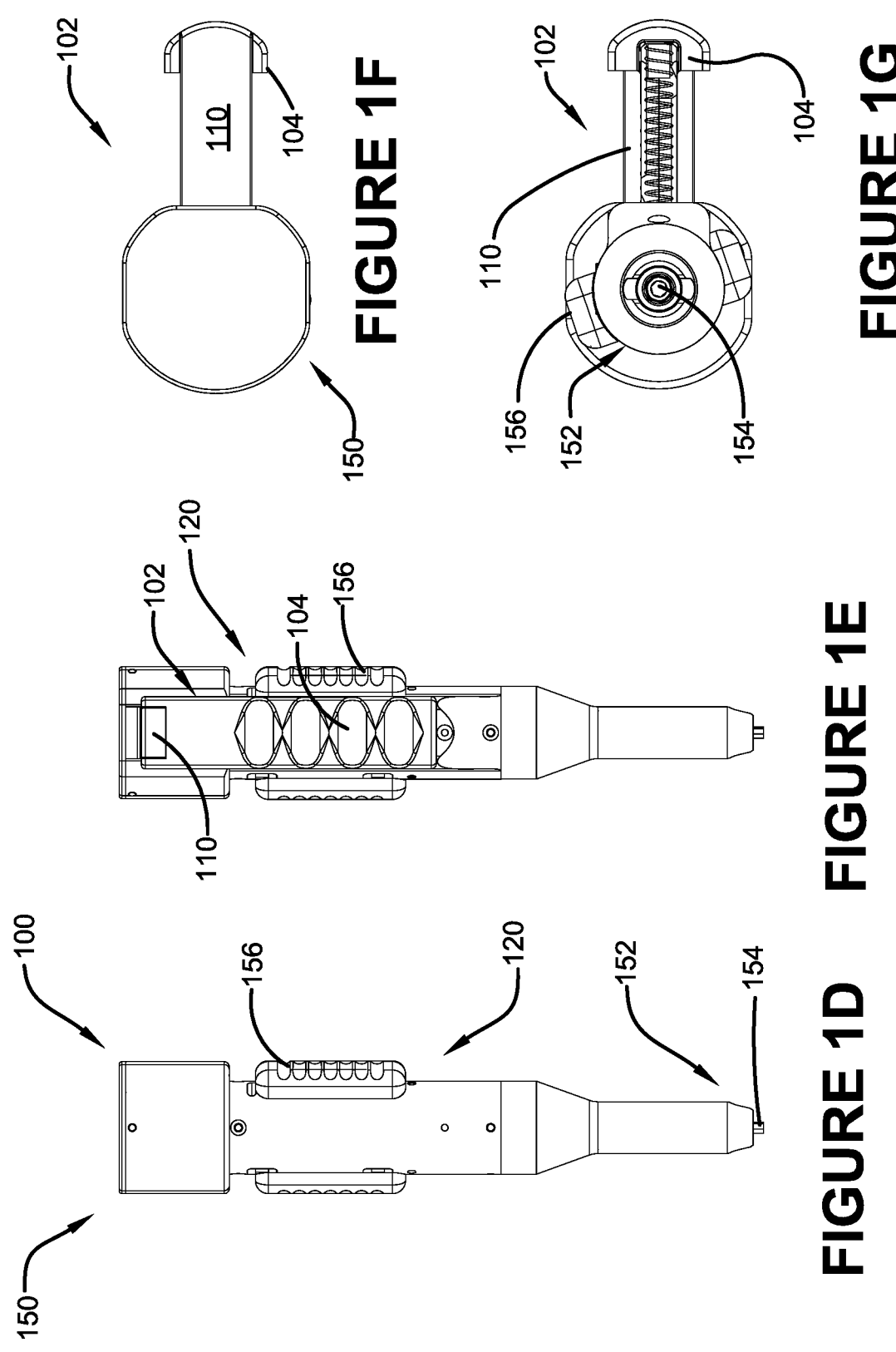
Figures 2A, 2B, 2C:
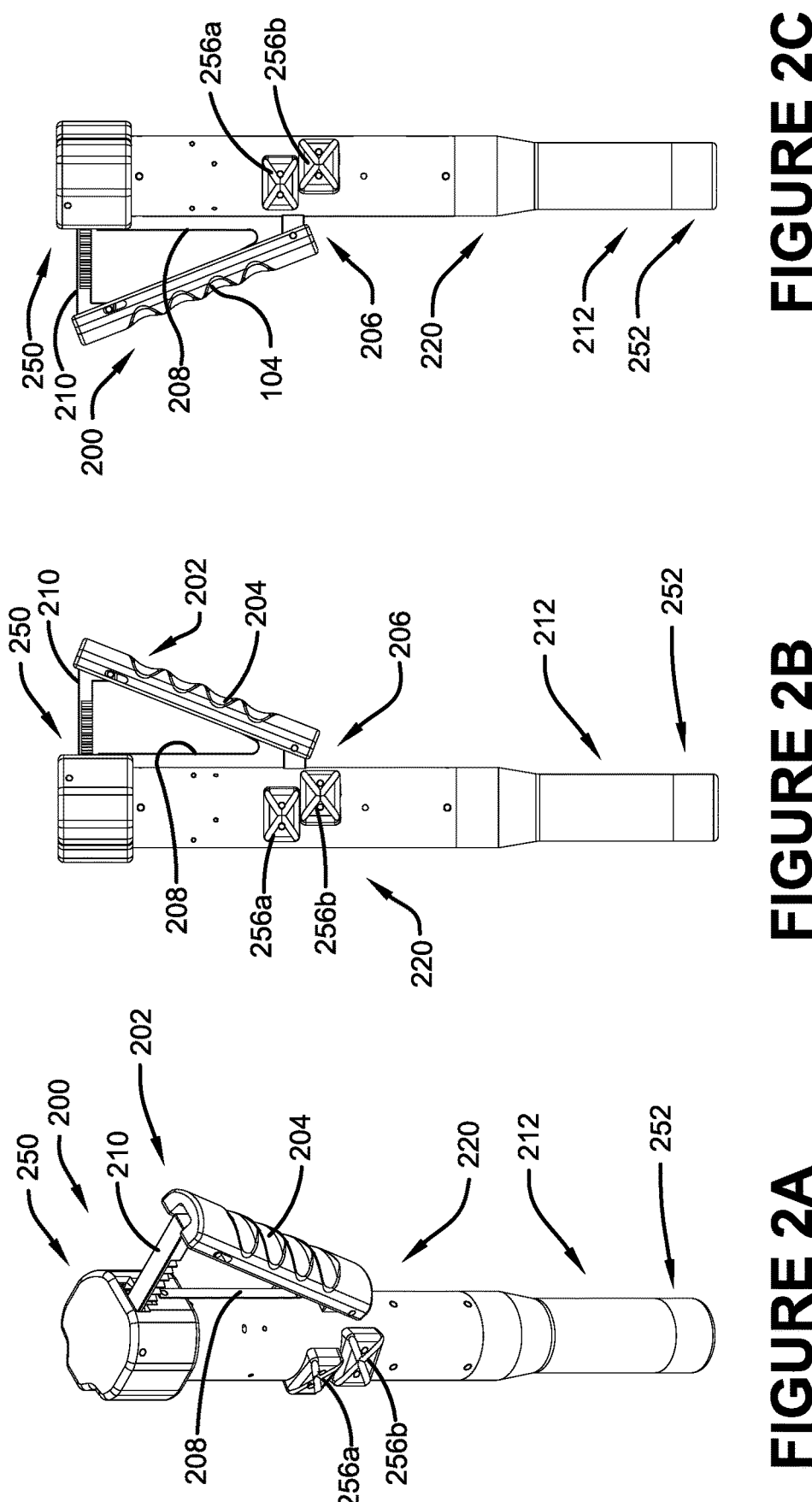
FIGS. 2A-2G are component diagram illustrating another example implementation of a fastener driving device that can be operated one-handed and can provide torque and counter-torque.
Figures 2D, 2E, 2F, 2G:
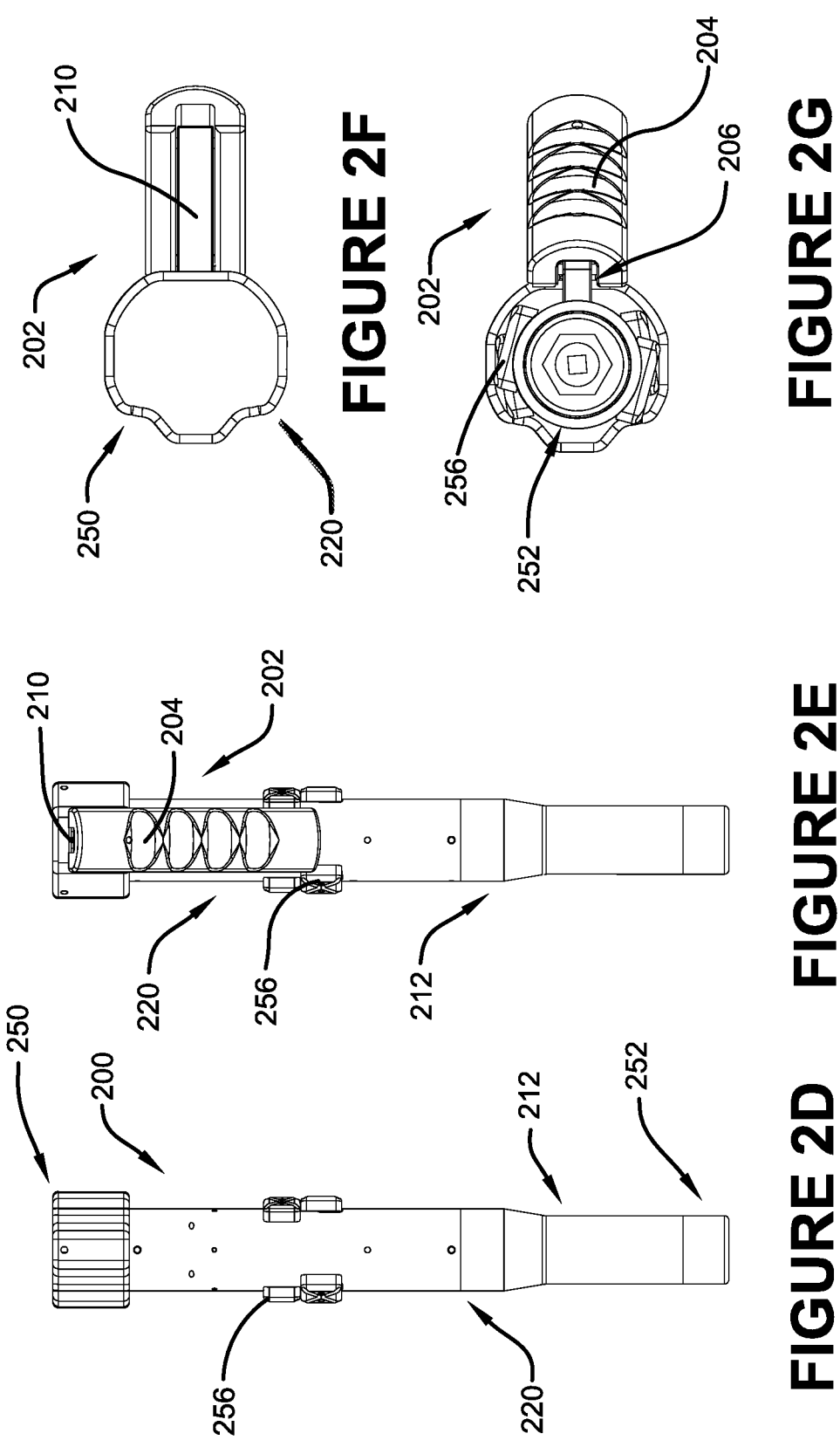

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are shown in block diagram form in order to facilitate describing the claimed subject matter.

In one aspect, a device that applies torque to a tool (e.g., fastener tool, drill, other rotating tools) disposed at the end of a rotating shaft can be used to drive a target component (e.g., fastener, auger, etc.) into a target base (e.g., surface, earth, other targeted parts). Further, in this aspect, a counter-torque component can be fixedly engaged with the housing and/or handle of the device, where the counter-torque component is designed to engage with the target base. In this way, for example, the base can be stabilized (e.g., have sufficient mass, and/or be fastened/fixed to a stabilizing mass) to mitigate rotation of the base with the target component to which it is engaged. In this example, the stabilization of the base can provide a counter-torque that is transferred to the device housing by way of the counter-torque component.

As one example, in this aspect, the exemplary device may allow a surgeon to use merely one hand to place a screw (e.g., tighten a set screw) in a spinal stabilization device, while it drives (e.g., applies the torque to) the set screw while also holding on to the spinal stabilizer or spinal rod to apply a counter torque to the device in place. As another example, the driver can be used to tighten a nut and bolt construct (e.g., or loosened) using merely one hand by applying a tightening torque to the nut, and a counter-torque to the bolt with the same driver. As another example, this device can be used to apply torque and counter-torque to different components at the same time while mitigating stresses, moments, or torques extending beyond the device, because substantially all stresses, torques and counter-torques are contained within the device. As another example, the driver can be used to screw a fastener into a substrate, while the counter-torque is applied to the substrate, for example screwing a screw into a substrate such as, but not limited to, bone, metal, or wood. As another example, an auger may be used to draw earth from the ground, while the housing of the device is engaged with the ground to apply counter-torque to stabilize the device.

FIGS. 1A-1G are component diagrams illustrating one example implementation of a device 100 for applying torque to a fastener (e.g., a threaded fastener, such as a screw or bolt) in a first direction while applying counter-torque in a second direction. In this way, for example, the threaded fastener can be driven into (e.g., or out of) a target base using the threads of the screw, while rotation of the target base and/or device 100 is mitigated. FIG. 1A is a isometric view, 1B is a first side view, 1C is a second side view, 1D is a front view, 1E is a rear view, 1F is a top view, and 1G is a bottom view.

As illustrated, the device 100 comprises a manually active actuator 102 disposed at a first end 150 (e.g., proximal end or upper portion) of the housing 120 of the device 100. The actuator 102 comprises a handle 104, actuator guide/support members 106, a biasing spring 108, and an activator gear 110. Further, at a second end 152 (e.g., distal end or lower portion) of the housing 120, a tool driving portion 112 is disposed. As will be disclosed further below, the tool driving portion 112 comprises a rotating component (e.g., shaft) that drives a target tool 154 (e.g., fastener bit), which, for example, may be of any particular design configured to operably interface with the target component (e.g., fastener). Additionally, one or more buttons or switches 156 can be disposed on the sides of the upper portion of the housing 120, and can be used, for example, to select rotation direction of the applied torque, as will be described further below.

FIGS. 2A-2G are component diagrams illustrating another example implementation of an alternate device 200 for applying torque to a target tool in a first direction while applying counter-torque in a second direction. The device 200 comprises housing 220, which houses various components of the device 200. Further, the device comprises a first end 250 (e.g., proximal end or upper portion) of the housing 220, and a second end 252 (e.g., distal end or lower portion) of the housing 220. Further, in this example implementation of the device 200, an manually operated actuator 202 comprises a handle 204, an actuator hinge/connection point 206, a biasing spring 208, and an activator gear 210. A tool driving portion 212 is disposed at the second end 252. Additionally, one or more buttons or switches 256 (256a, 256b, and so on) can be disposed on the sides of the upper portion 250 of the housing 220 and can be used to select rotation direction of the applied torque, and/or change an amount of torque/rotation applied, as will be described below.

Figure 3B:
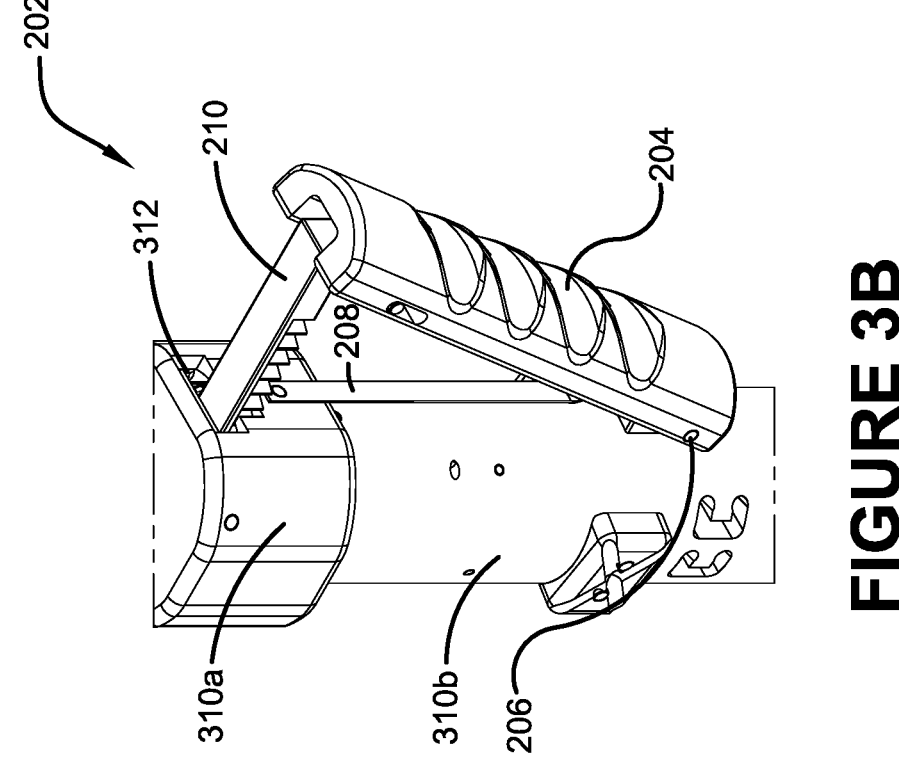
FIGS. 3A and 3B are component diagram illustrating two example implementations of alternate means for activating the tool driver device.
Figure 3A:
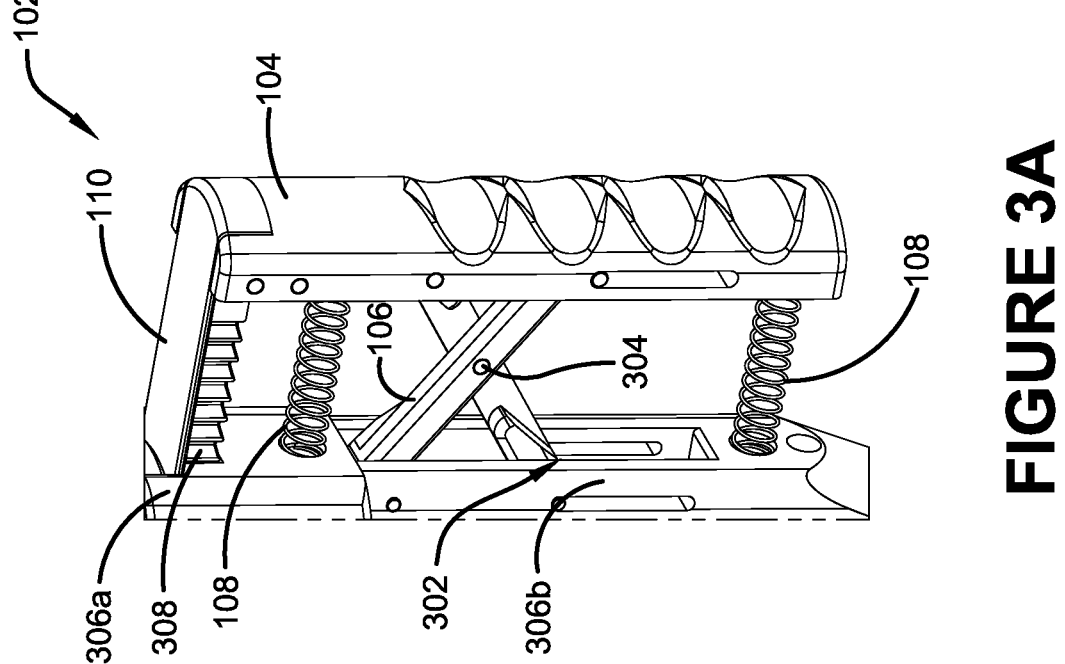

FIGS. 3A and 3B are component diagrams, in a perspective view, of two different alternate designs of the manually operated actuator 102, 202 of the example devices 100, 200. With continued reference to FIGS. 1 and 2, as described above, in FIG. 3A, the actuator 102 of device 100 comprises a handle 104, guide members 106, biasing springs 108, and the activator gear 110. Further, in this implementation, the guide members 106 are coupled together at a pivot point 304 to provide a scissor-type action. In this implementation, the guide members 106 ride in channels 302 in the lower handle housing 306b of the upper portion 150 of the device 100, for example, and slide up and down when the handle 104 is compressed and released. Additionally, the biasing springs 108 can provide a biasing force away from the lower handle housing 306b to return the handle 104 to its starting position (as shown) when compression is removed. As an example, when the handle 104 is compressed the activator gear 110 is translated into the upper handle housing 306a through an actuator opening 308 in the upper handle housing 306a. In this example, when the handle 104 is released the biasing springs 108 provide the biasing force to return the handle 104, and the activator gear 110 to their starting positions (e.g., as illustrated).

In FIG. 3B, the actuator 202 of the device 200 comprises a handle 204, a hinge/connection point 206, a biasing spring 208, and an activator gear 210. Further, in this implementation, the hinge/connection point 206 couples the handle 204 with the lower handle housing 310b of the device 200 in a pivotal arrangement. In this way, for example, the hinge/connection point 206 can stabilize the handle 204 when it is compressed and returned to its starting position (as shown), while providing a pivot point for the linear force applied to the activator gear 210 by the handle 204. Additionally, as illustrated, when the handle 204 is compressed the activator gear 210 is driven into an opening 312 in the upper handle housing 310a; and, when the compressive force applied to the handle 204 is released the biasing spring 208 applies a biasing force that can return the handle 204 (e.g., and activator gear 210) to its starting (uncompressed) position. As illustrated, in this implementation, the biasing spring 208 can be fixedly engaged with the housing 310a or 310b and with the handle 204. In this example, the biasing spring is formed from a single band suitable material (e.g., metal, polymer, carbon fiber, etc.) disposed in a "U" or "V" shape. However, it is anticipated that any suitable design may be employed, where the biasing force is applied in a direction that operably separates (e.g., drives apart) the handle 204 from the housing 310a.

Figure 4B:
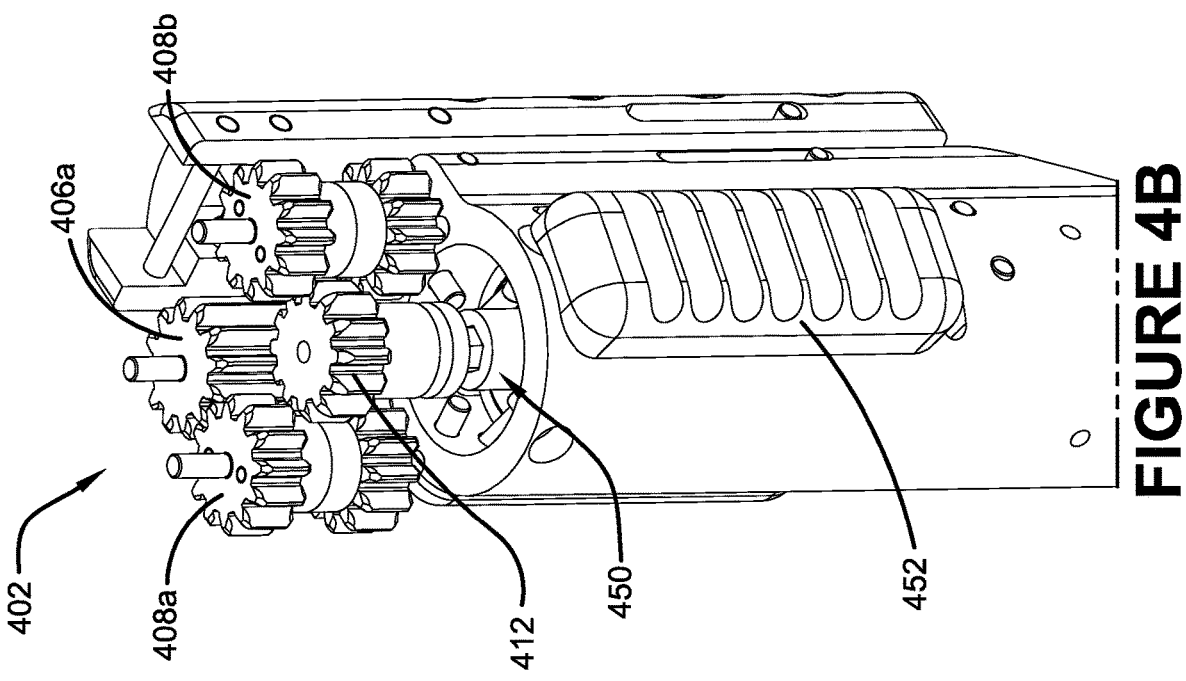
FIGS. 4A-4D are component diagram illustrating example implementations of one or more portions of the one or more systems and devices described herein.

FIGS. 4A-4D are component diagrams that illustrate various example implementations of a power input drive 402 in a first position (e.g., with a center rack gear 410 shown in FIGS. 4A, 4C, 4D), and a second position (shown in FIGS. 4B, center rack 410 not shown for better visibility). In this implementation, power input drive 402 is of a rack and spur gear design, with a slidable center rack gear 410 (e.g., the activator gear 110, 210), which is attached to and translates linearly within the ratchet mechanism box 404 portion of the upper handle housing (e.g., 306a, 310a); and further engages with one or more spur gears (such as 406a, 406b (not shown for better visibility), 408a, 408b). Further, the rack and spur gear design of the power input drive 402 can be combined with reversible mechanism that can reverse the direction of rotation of the drive, as shown in FIG. 4B, by translating switch 452 (e.g., or 156) upward. In this way, the driving of the center rack gear 410 into the power input drive 402, for example, can result in the drive rotating clockwise in a first position of switch 452 and thereby drive shaft gear 412 (FIGS. 4A, 4C, 4D), and counterclockwise in a second position (FIG. 4B).

Figure 4A:
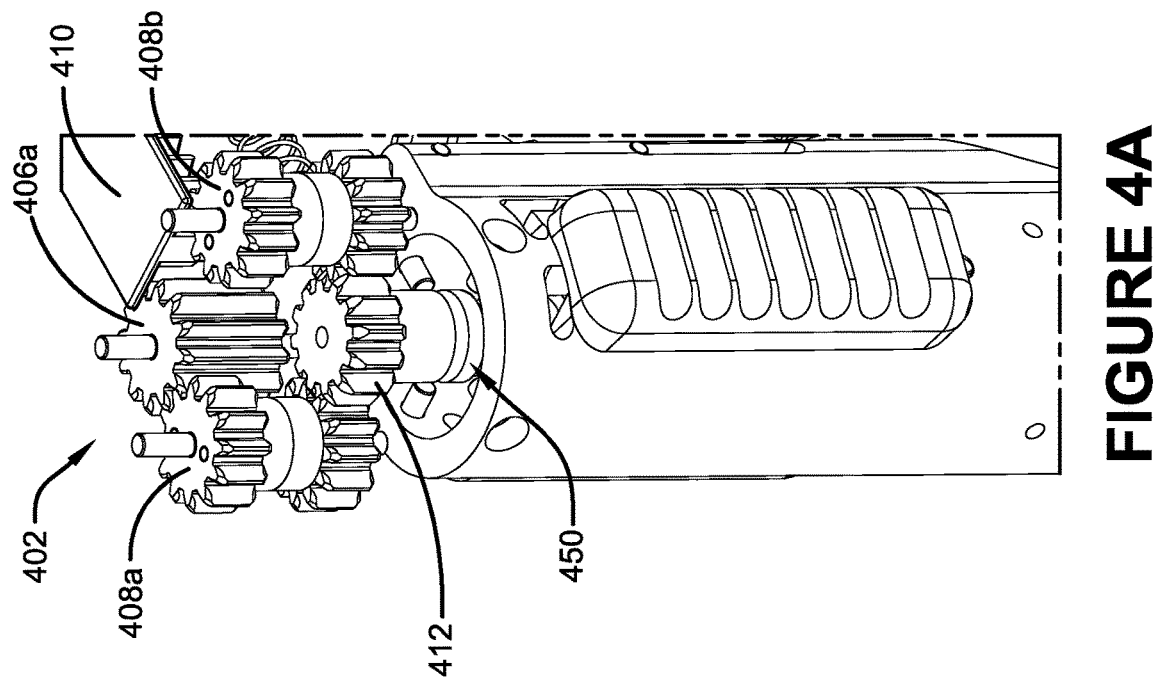
Figures 4C, 4D:
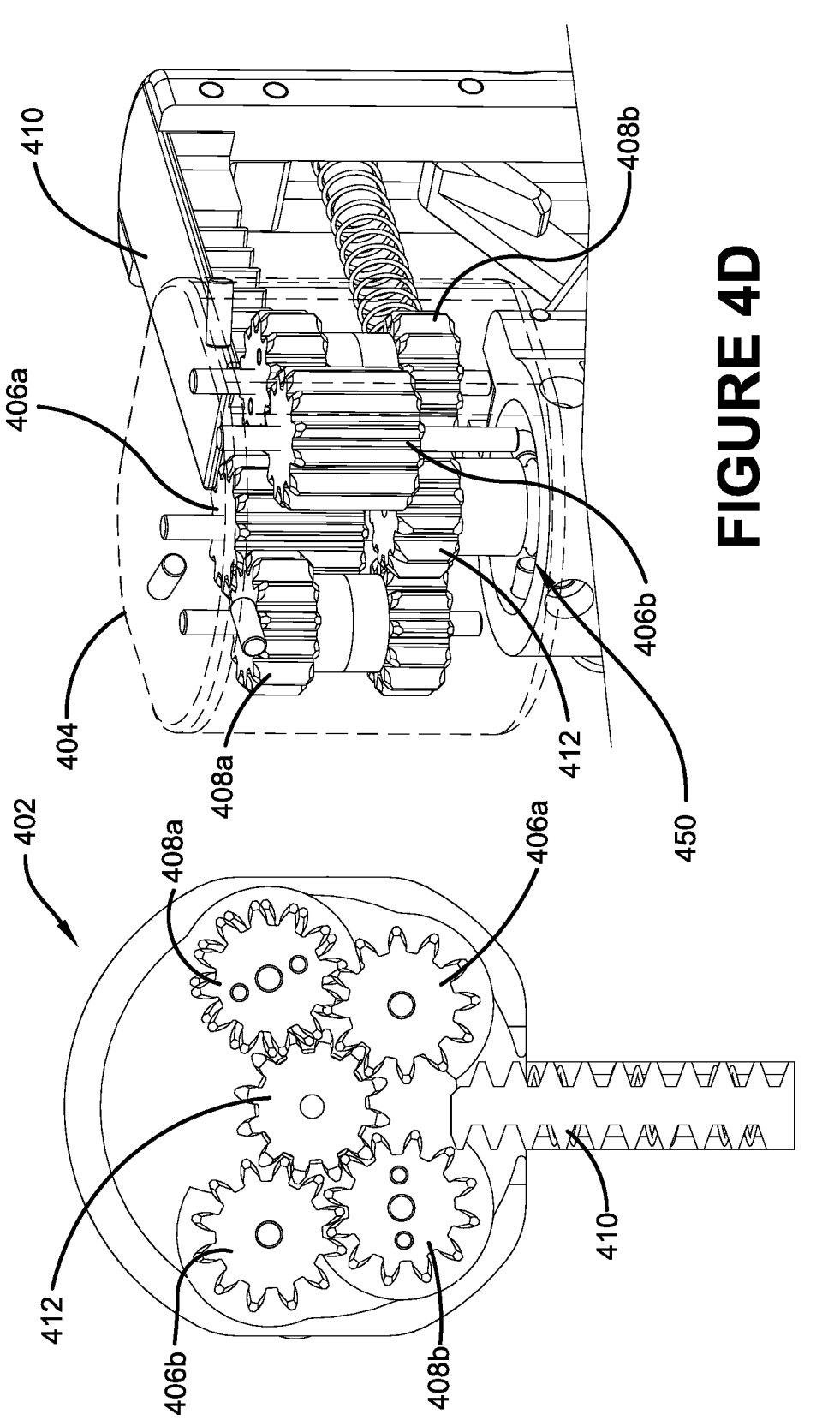

In these examples, when the center rack gear 410 is driven into the power input drive 402 (e.g., from the first position to the second position), the gear teeth on the center rack gear 410 meshably engage with one or more initial spur gears 406a, 406b. In this example, as illustrated in FIGS. 4A, 4C and 4D, in a first position, the initial spur gears 406a, 406b will rotate, respectively, in a clockwise and counterclockwise direction. Spur gear 406a meshably engages secondary spur gear 408a resulting in a counterclockwise rotation. Finally, the lower portions of initial spur gear 406b and secondary spur gear 408a meshably engage with drive shaft gear 412 resulting in the drive shaft 412 to be rotated in a clockwise direction, when the handle 104 is compressed. As illustrated in FIG. 4B, the drive shaft gear 412 can be disposed in a second position, such as an up position, which may be selected by activating (e.g., translating up) a selection switch 452 (e.g., 156 of FIG. 1). In the second position, the drive shaft gear 412 is disengaged from the secondary spur gear 408a, and initial spur gear 406b, and is meshably engaged with the initial spur gears 406a, and secondary spur gear 408b, which is meshably engaged with initial spur gear 406b. In this way, when the gear teeth on the center rack gear 410 rotate the initial spur gear 406a and secondary spur gear 408b, respectively, in the clockwise and counterclockwise direction, the meshably engaged drive shaft gear 412 will be rotated in the counterclockwise direction, when the handle 104 is compressed.

Figures 5A, 5B:
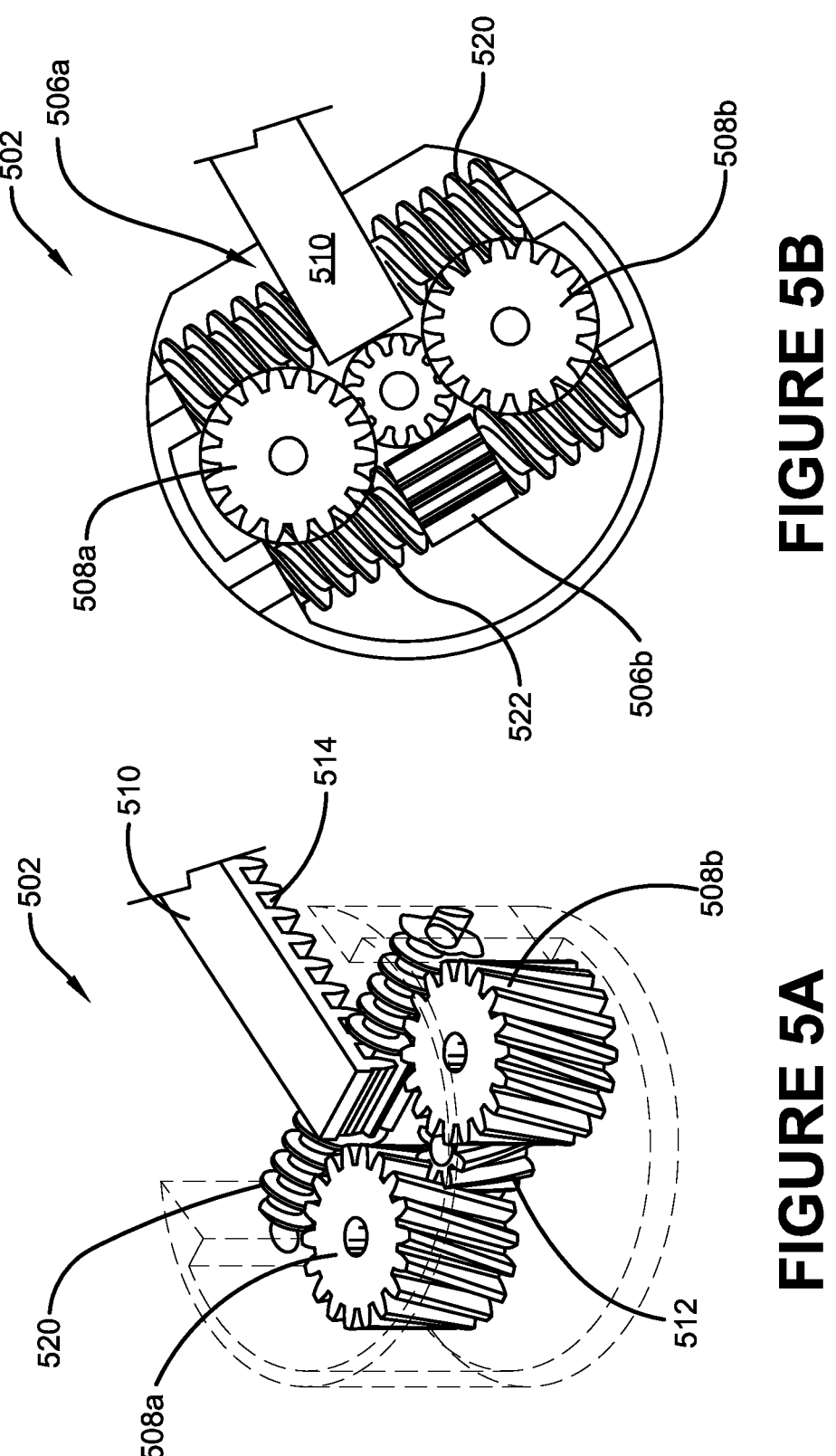
FIGS. 5A and 5B are component diagram illustrating an alternate example implementation of one or more portions of the one or more systems and devices described herein.

FIGS. 5A and 5B show an alternate arrangement of a power input drive 502. As illustrated, in this implementation, the gear teeth 514 of the center rack gear 510 meshably engage with a first initial spur gear 506a that rotates in a horizontal axis. The first initial spur gear 506a is centrally fixed to a first worm gear 520 that rotates around the horizontal axis of the first initial spur gear 506a. As such, when the center rack gear 510 is driven into the power input drive 502 (e.g., by compressing the handle 104) the first initial spur gear 506a and first worm gear 520 rotate in a first direction (e.g., counterclockwise when viewed from a side view of the thread of the worm gear). The first worm gear 520 is meshedly engaged with one or more secondary spur gears 508a, 508b, which will rotate in a counterclockwise direction when the first worm gear 520 rotates in the first direction. A drive shaft gear 512 is disposed between the secondary spur gears 508a, 508b, and rotates in a clockwise direction, which in turn rotates the drive shaft in a clockwise direction, when the handle 104 is compressed.

Alternately, as illustrated in FIG. 5B, a second worm gear 522 with a second initial spur gear 506b can be meshedly engaged with the center rack gear 510, such by activating a selection switch or button, which simultaneously deactivates the first worm gear 520. In this example, when the second worm gear 522 is activated, the second initial spur gear 506b rotates in a clockwise direction, which rotates the second worm gear 522 in a clockwise direction, which, based on the thread arrangement, results in the secondary spur gears 508a, 508b rotating in a clockwise direction. In this way, the engaged drive shaft gear 512 will rotate in a counterclockwise direction, as will the drive shaft, when the handle 104 is compressed. It may be appreciated that a power source may be powered manually, by electric motor, pneumatic drive, hydraulic drive, or any other suitable means.

Figure 6:
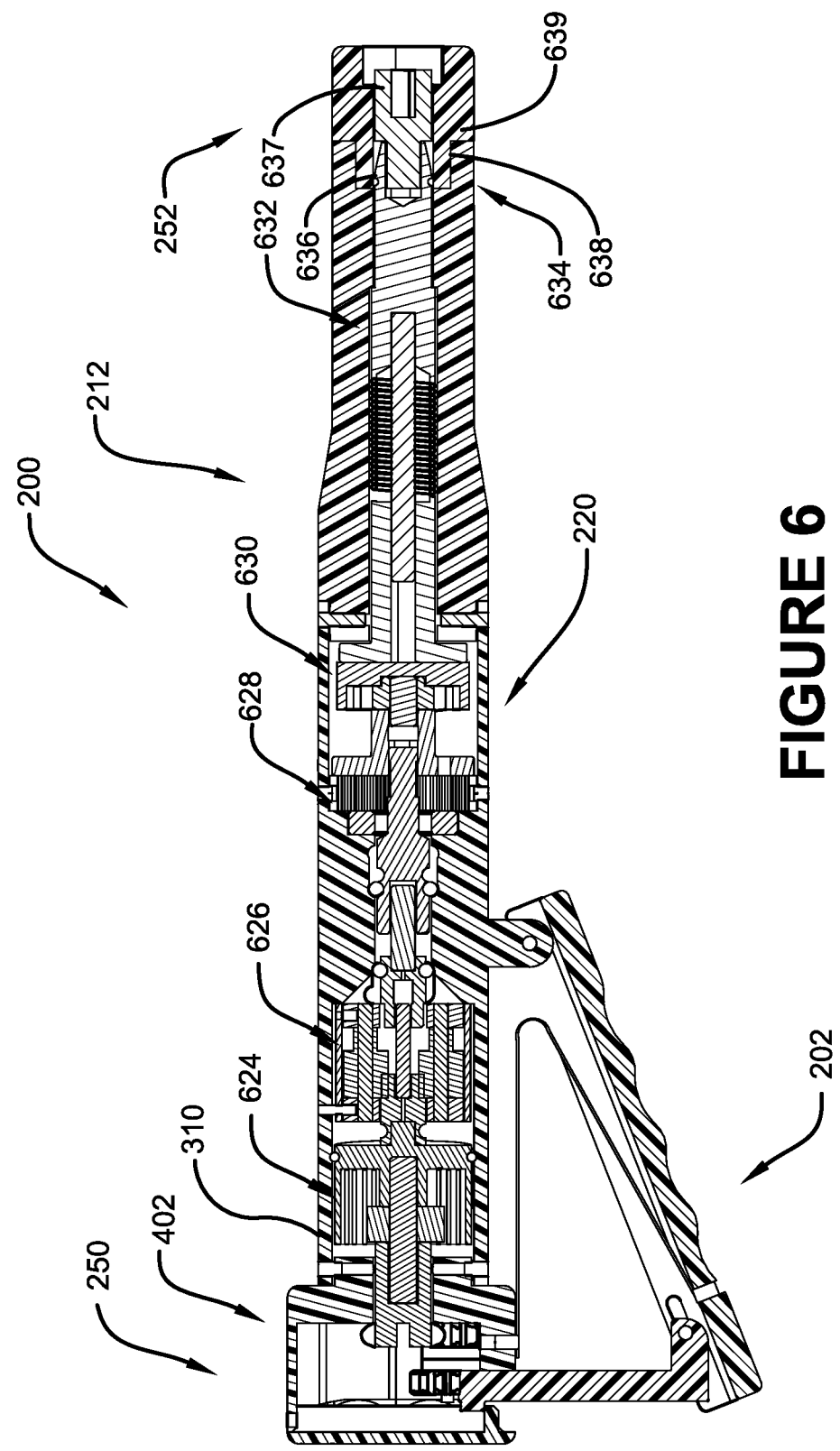
FIG. 6 is a component diagram illustrating a cut-away view of one exemplary implementation of a fastener driving device that can be operated one-handed and can provide torque and counter-torque.

FIG. 6 is a cutaway view of the example tool driver device 200. The example device 200 comprises the first end 250, the second end 252, the actuator 202, power input drive 402 (e.g., or 502), and housing 220, as described above. Further, the example device 200 comprises a ratcheting mechanism 624, a rotation reversal mechanism 626, a torque conversion mechanism 628, a torque limiter 630, a rotating drive shaft 632 (e.g., retractable), and a counter-torque component holder 634 (e.g., sleeve for holding a counter-torque tip), along with a drive tip holder 636 (e.g., which may be formed as a part of the rotating shaft 632, or a separate component at the distal end of the shaft). The counter torque component holder 634 can comprise a comprise a distal end 638 that is formed to operably hold a counter torque component 639

(e.g., counter-torque tool, such as a female hex-shaped). The drive tip holder 636 and counter torque component holder's distal end 638 can be configured to selectably accept different types of driver tools 637 and counter torque component 639 (e.g., tools), respectively. As an example, the rotating drive shaft 632, using the drive tip holder 636, can selectably engage with a first drive tool, and selectably engage with a second, different drive tool. Further, the counter torque component holder 632 can selectably engage with a first counter-torque component (e.g., tool), and selectably engage with a second, different counter-torque component (e.g., tool).

Figure 7B:
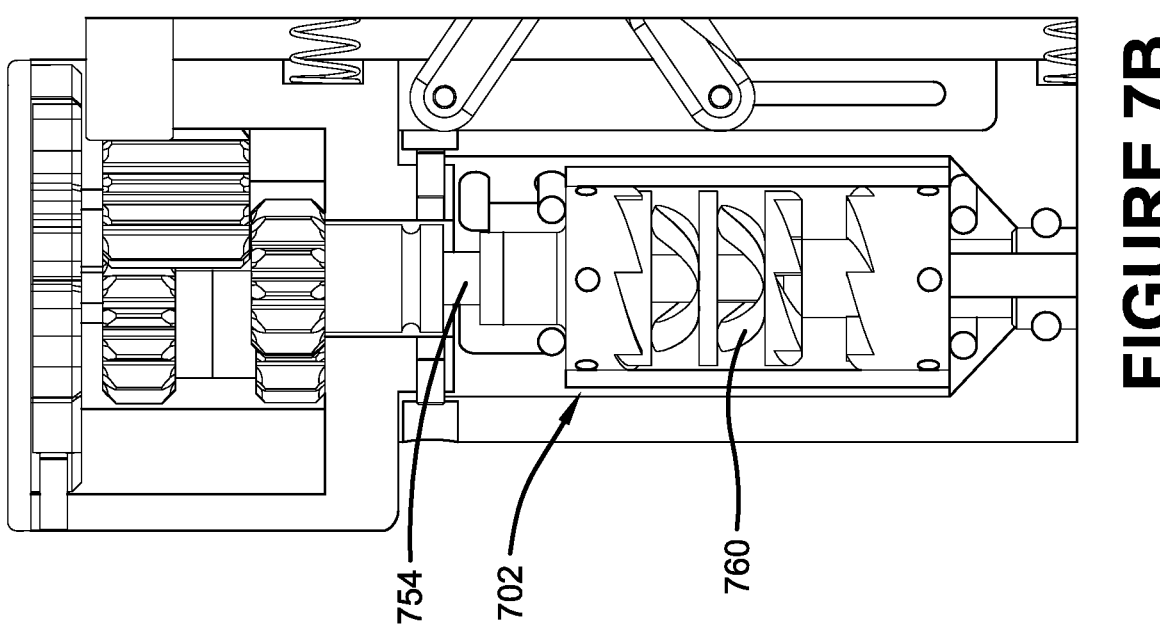
FIGS. 7A-7C are component diagram illustrating example implementations of one or more portions of the one or more systems and devices described herein, where a direction of the applied torque can be controlled.
Figure 7A:
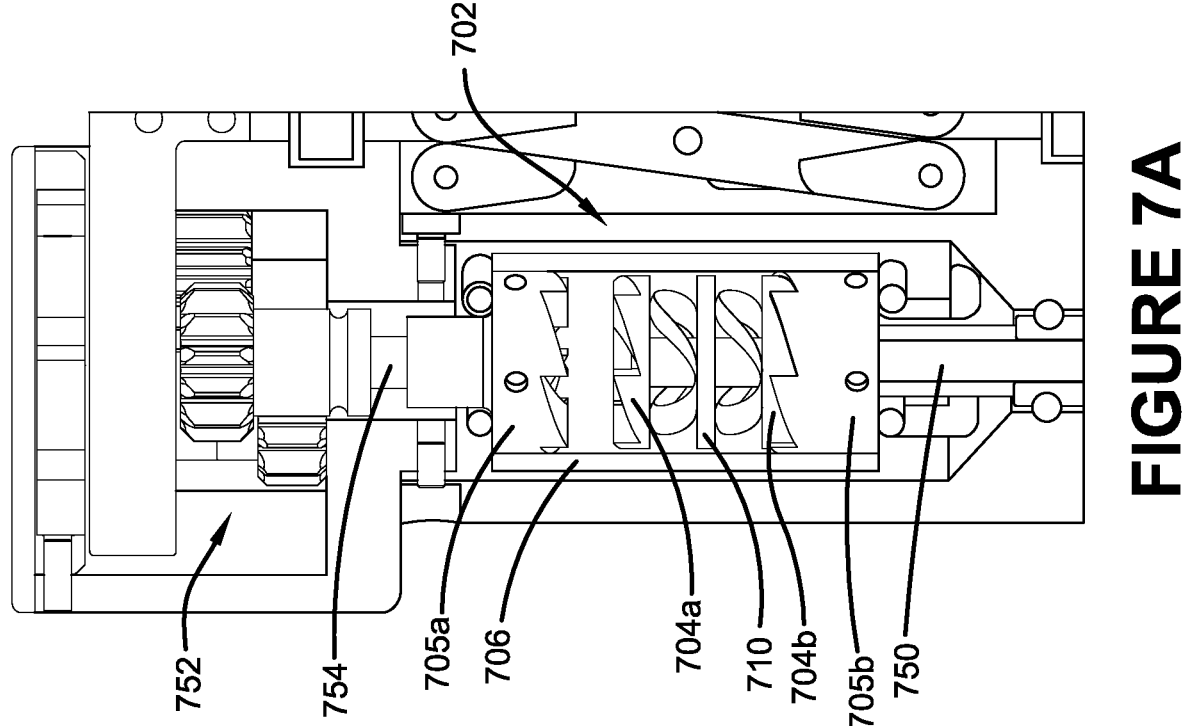
Figure 7C:
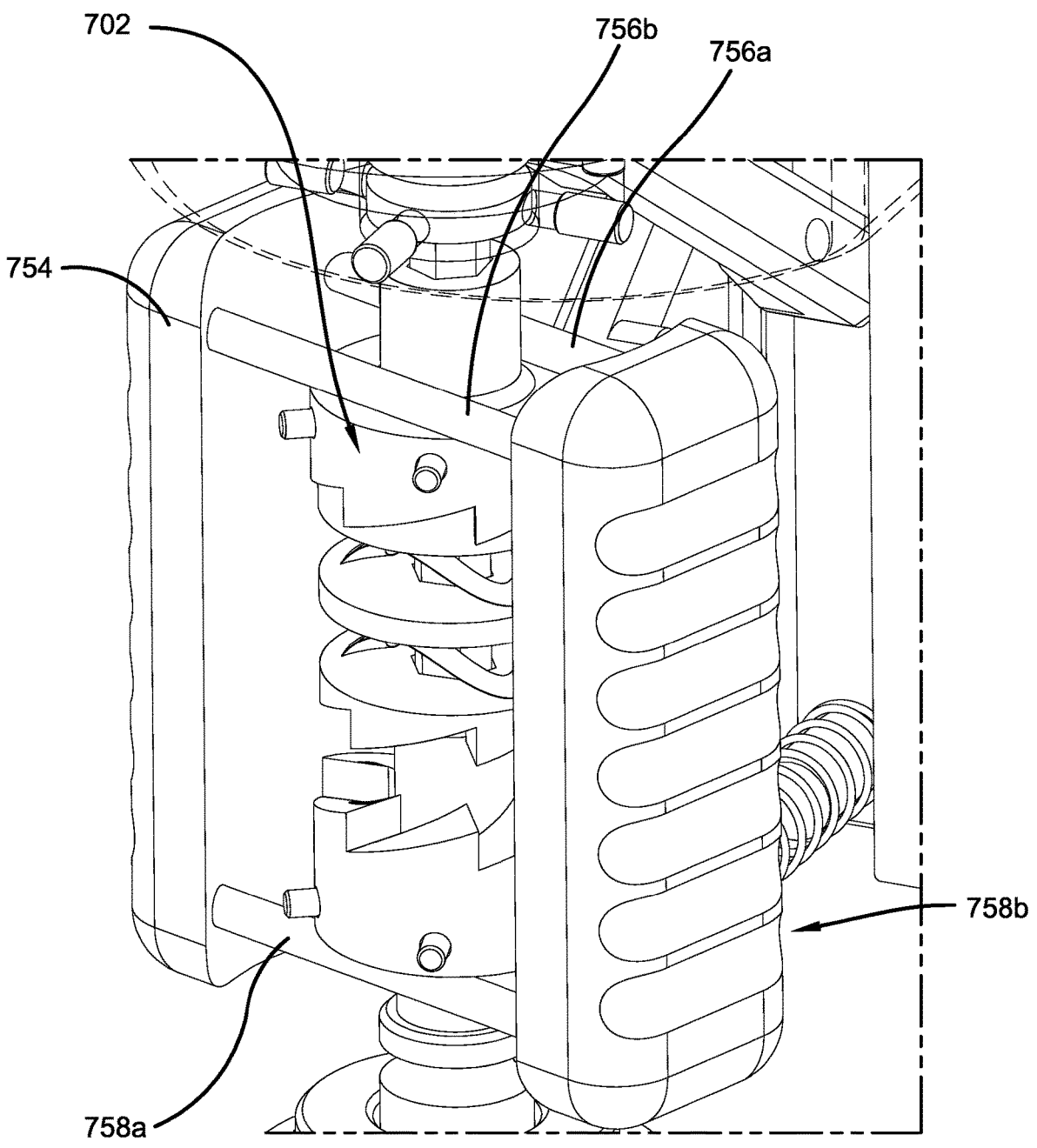

In some implementations, a ratcheting mechanism 624 may be provided to allow rotation in a first direction while mitigating rotation in a second direction. In one implementation, as illustrated in FIGS. 7A-7C, a ratcheting mechanism 702 may be selectably reversible, to allow for rotation in either rotational direction (e.g., while mitigating opposite rotation). FIG. 7A shows the ratcheting mechanism 702 in a first position, and FIGS. 7B and 7C show the ratcheting mechanism in a second position. In the first position, in this example, the drive shaft 754 from the power input drive 752 (e.g., 402, 502 in FIGS. 4 and 5) can be rigidly connected to the casing or body 706 of the ratcheting mechanism 702, and thereby drive pawls 705a and 705b. In the first position the driving pawl 705b of the ratcheting mechanism 702 rotates the lower driven pawl 704b, which then drives the drive shaft 750 in a counterclockwise direction. When the ratcheting mechanism 702 is selectably switched to the alternate position, for example, by translating the switch 156 to an upward position (e.g., first position in FIG. 7A), the drive shaft 750 is allowed to rotate in a counterclockwise rotation (e.g., unscrewing). When the ratcheting mechanism 702 is selectably switched by translating the switch 156 to a downward position (e.g., second position in FIGS. 7B and 7C), the upper driving pawl 705a of the ratcheting mechanism 702 rotates the upper driven pawl 704a, and the drive shaft 750 is allowed to rotate in a clockwise rotation (e.g., screwing in or driving into a target component). Wave springs or washers 760 can be disposed between a static disc 710 and the upper/lower "driven" pawls 704a, 704b, to allow ratcheting in the desired direction of rotation due to teeth on discs.

As illustrated in FIG. 7C, a slide switch 754 (e.g., 156 of FIG. 1, or the like) can be activated by sliding up or down. In this implementation, the slide switch 754 is fixed to a pair of pins above 756a, 756b and below 758a, 758b the ratcheting mechanism 702. The pins 756a, 756b, 758a, 758b are engaged with ratcheting mechanism 702 to translate it within the housing, e.g., up and down) along the drive shaft which may also move the drive shaft gear (e.g., 412), for example, up and down in the power input drive 402 or 752.

Figures 8A, 8B:
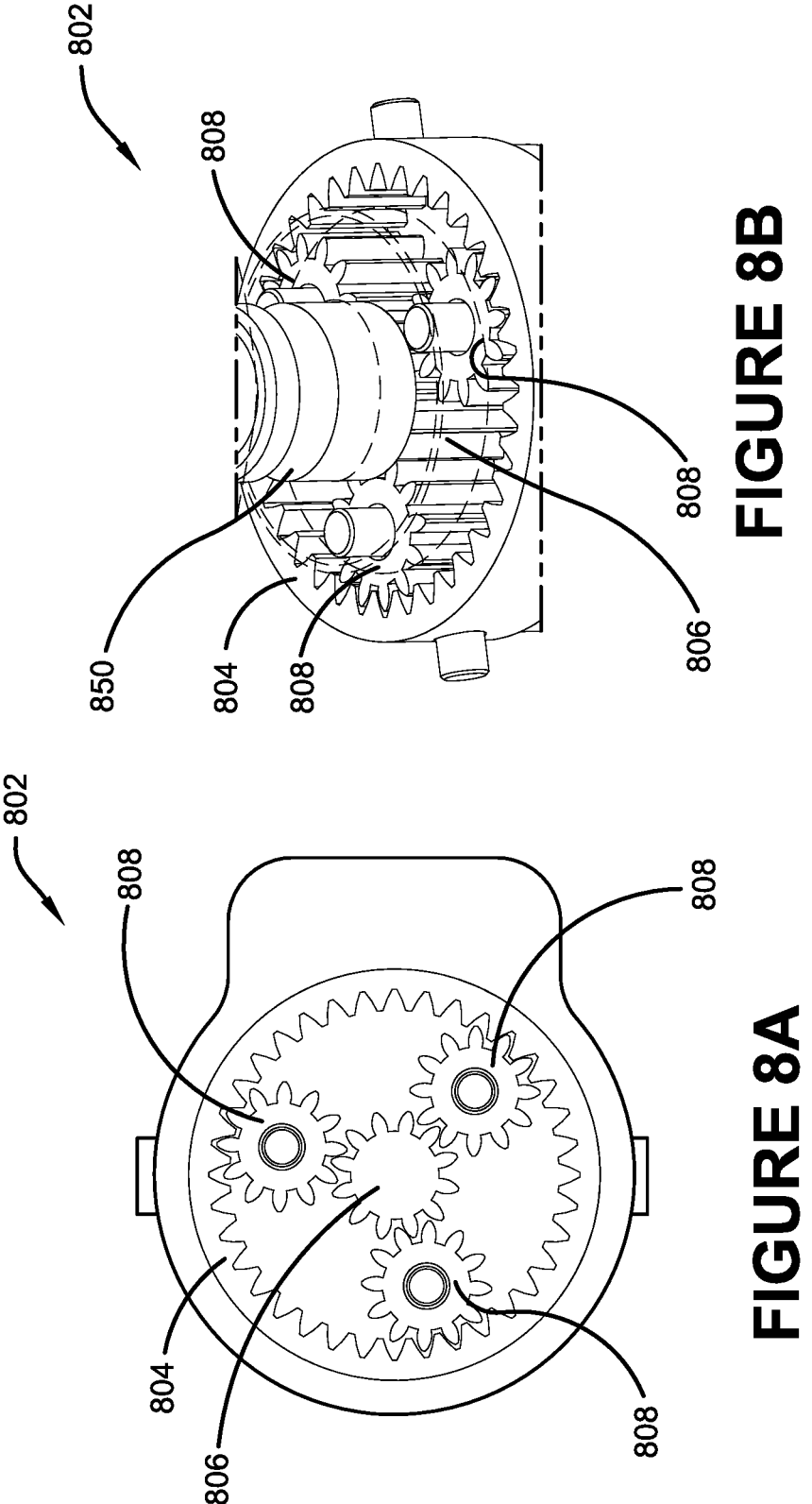
FIGS. 8A-8H are component diagram illustrating example implementations of one or more portions of the one or more systems and devices described herein, where an amount of torque applied can be controlled.
Figures 8C, 8D:
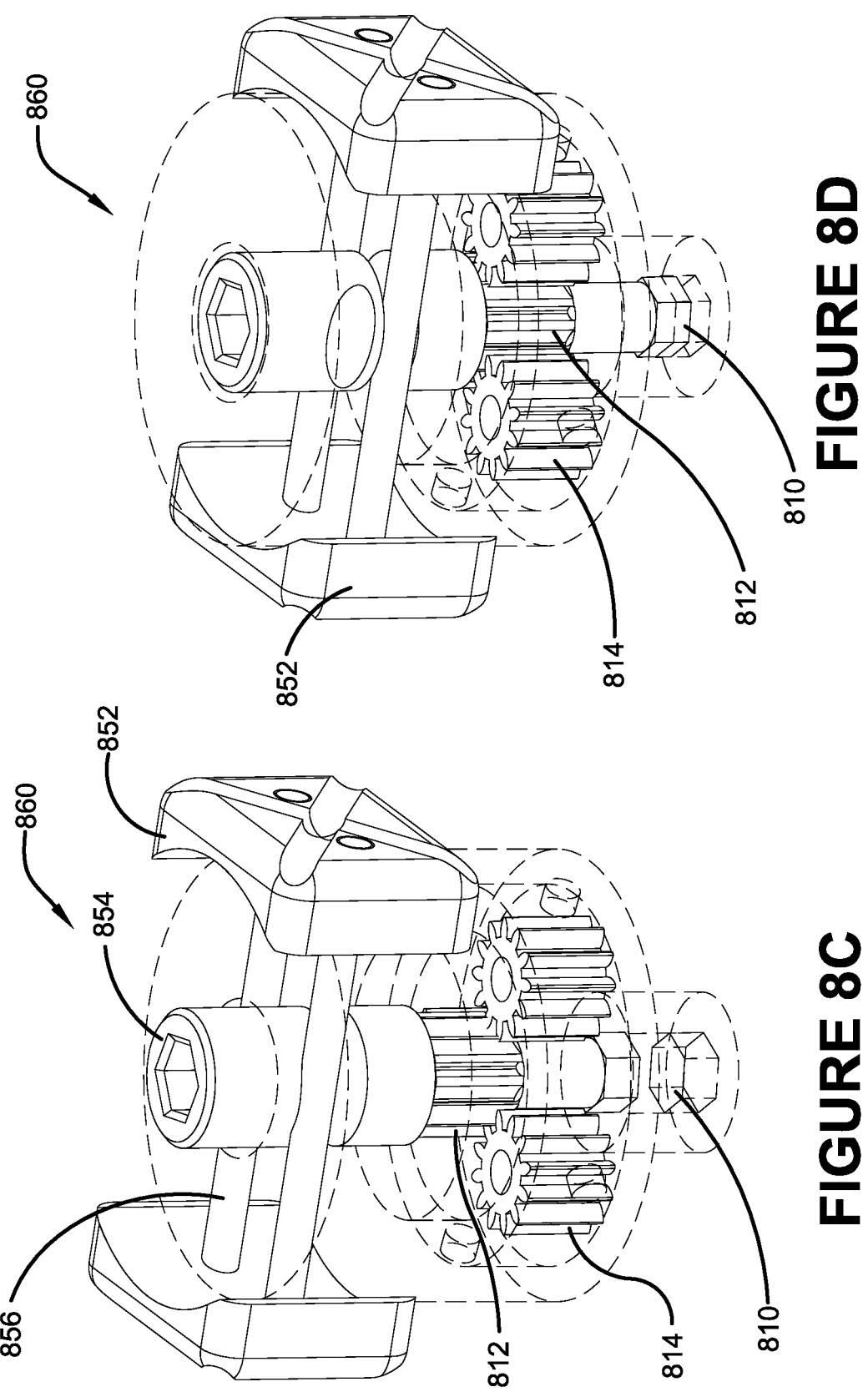
Figure 8F:
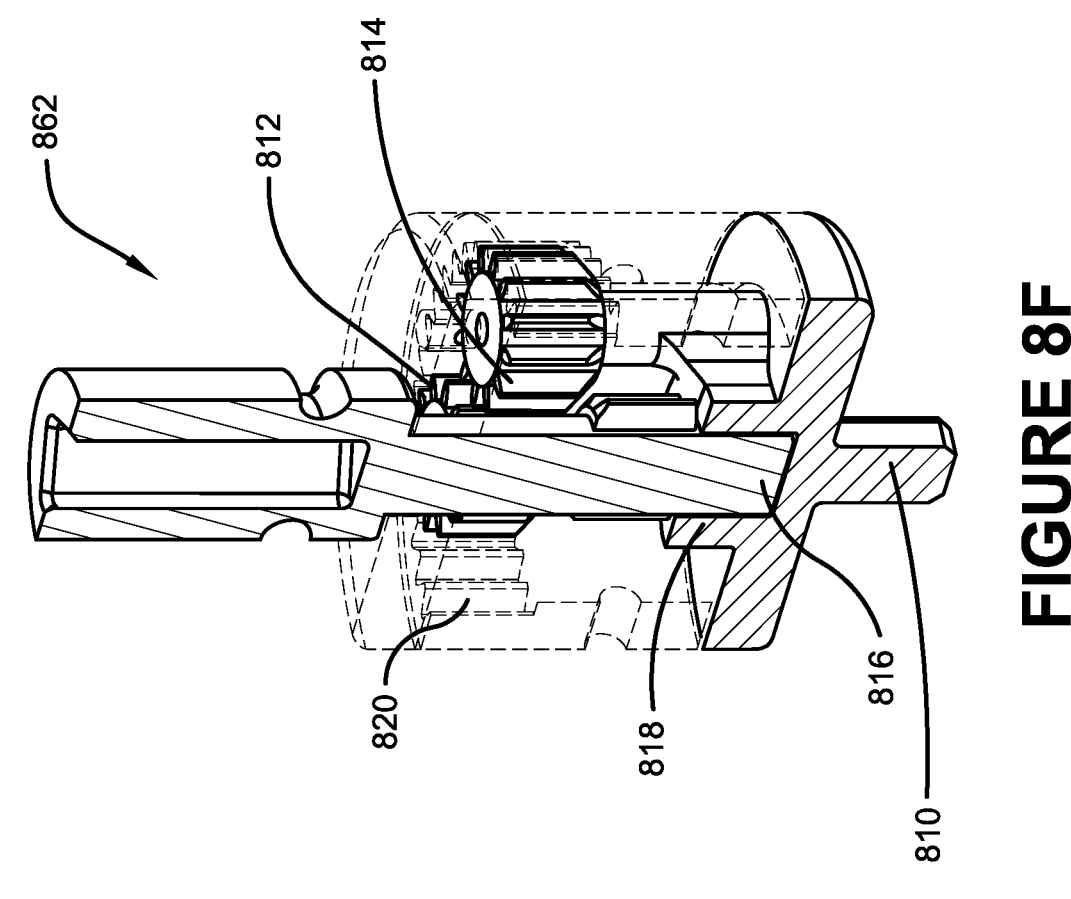
Figure 8E:
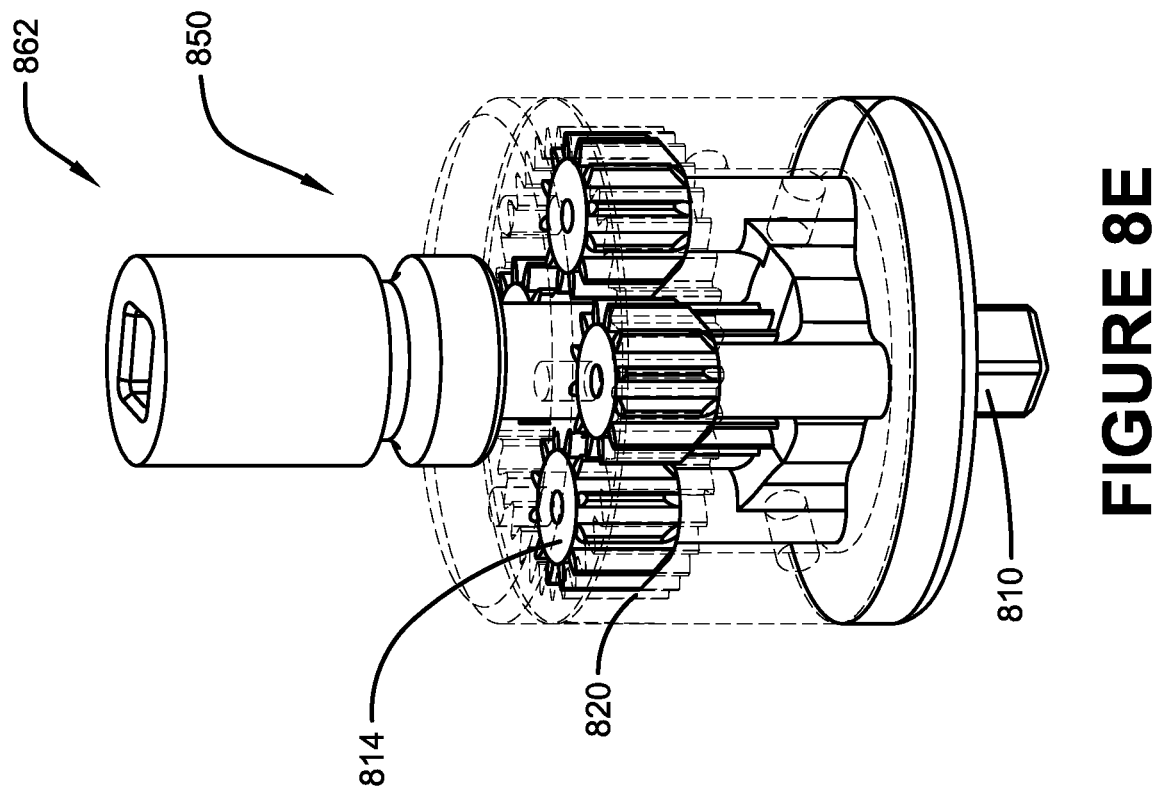
Figure 8H:
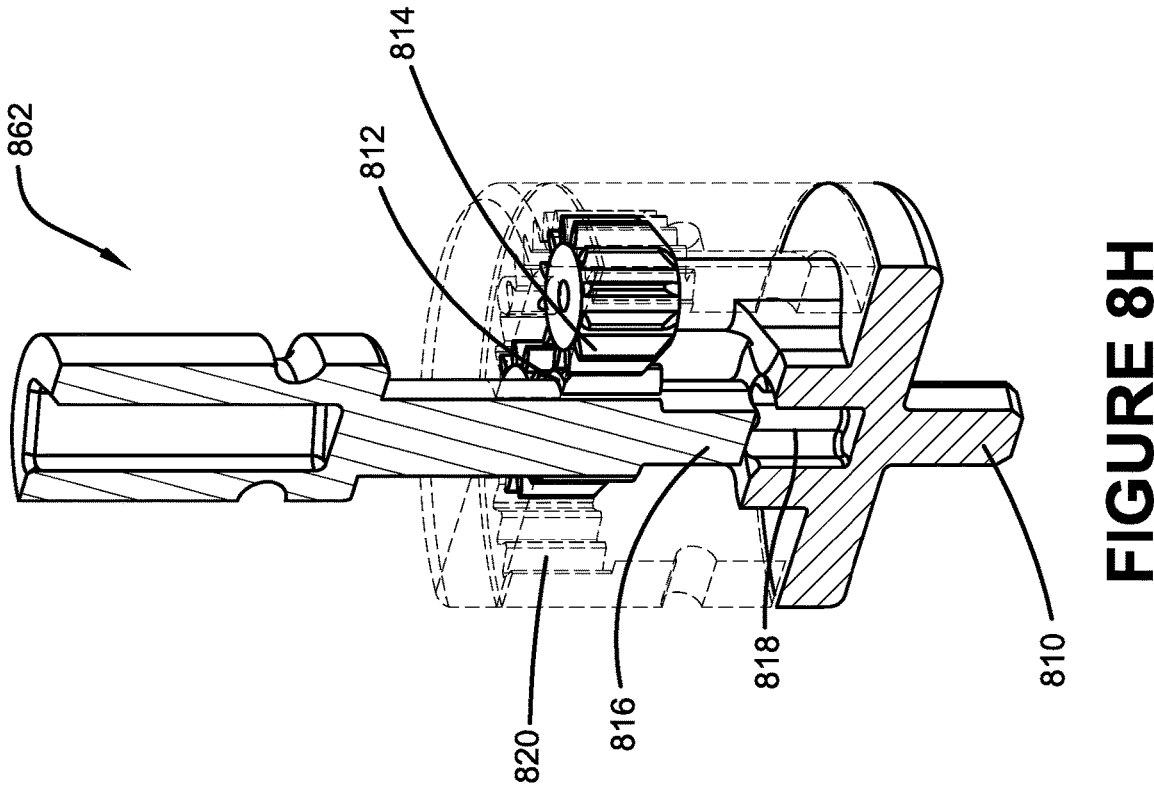
Figure 8G:
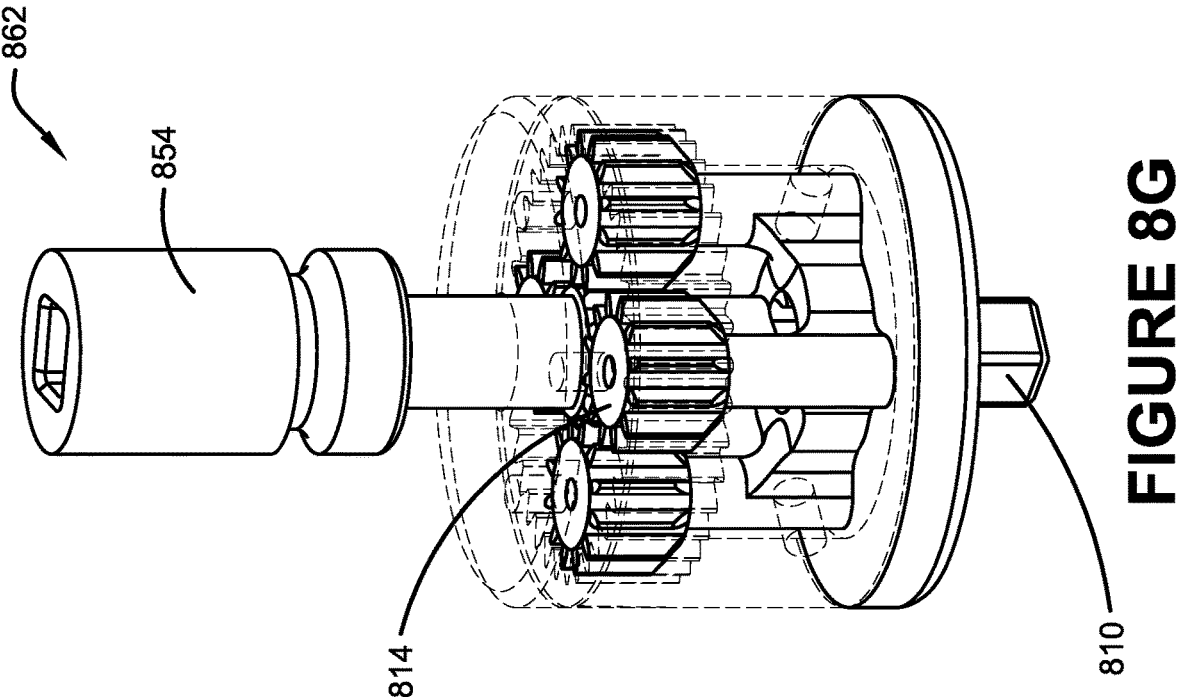
Figures 9, 10:
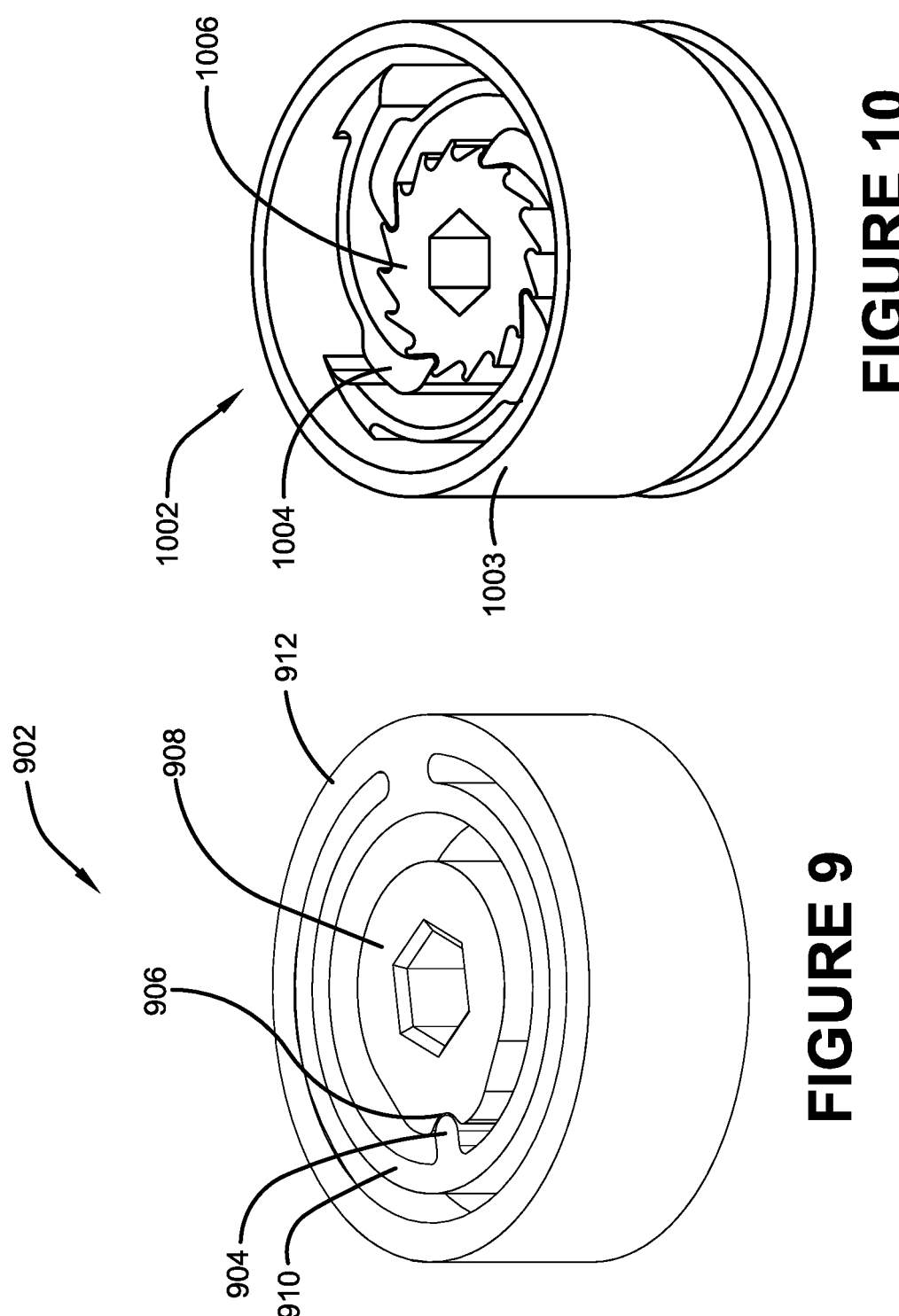
FIG. 9 is a component diagram illustrating an example implementation of one or more portions of systems and devices described herein, such as a torque limiter component.
FIG. 10 is a component diagram illustrating an example implementation of one or more portions of systems and devices described herein, such as a ratcheting directional control.

As illustrated in FIG. 10, an alternate ratcheting mechanism 1002 may be utilized. In this implementation, the inner spur gear 1006 is driven by the power drive shaft (e.g., 754 of FIG. 7A, 7B; or 750) from the power input drive 402 (e.g., or 502 or 752). Multiple flexible tabs 1004 can engage and transfer the rotational torque to the outer housing 1003, which is rigidly connected to the drive shaft (not shown, e.g., 850 of FIG. 8B). In some implementations, the ratcheting mechanism 1002 can be inverted, so that the outer housing 1003 is driven by the power drive shaft and the inner spur gear 1006 is connected to the drive shaft.

Figures 11A, 11B:
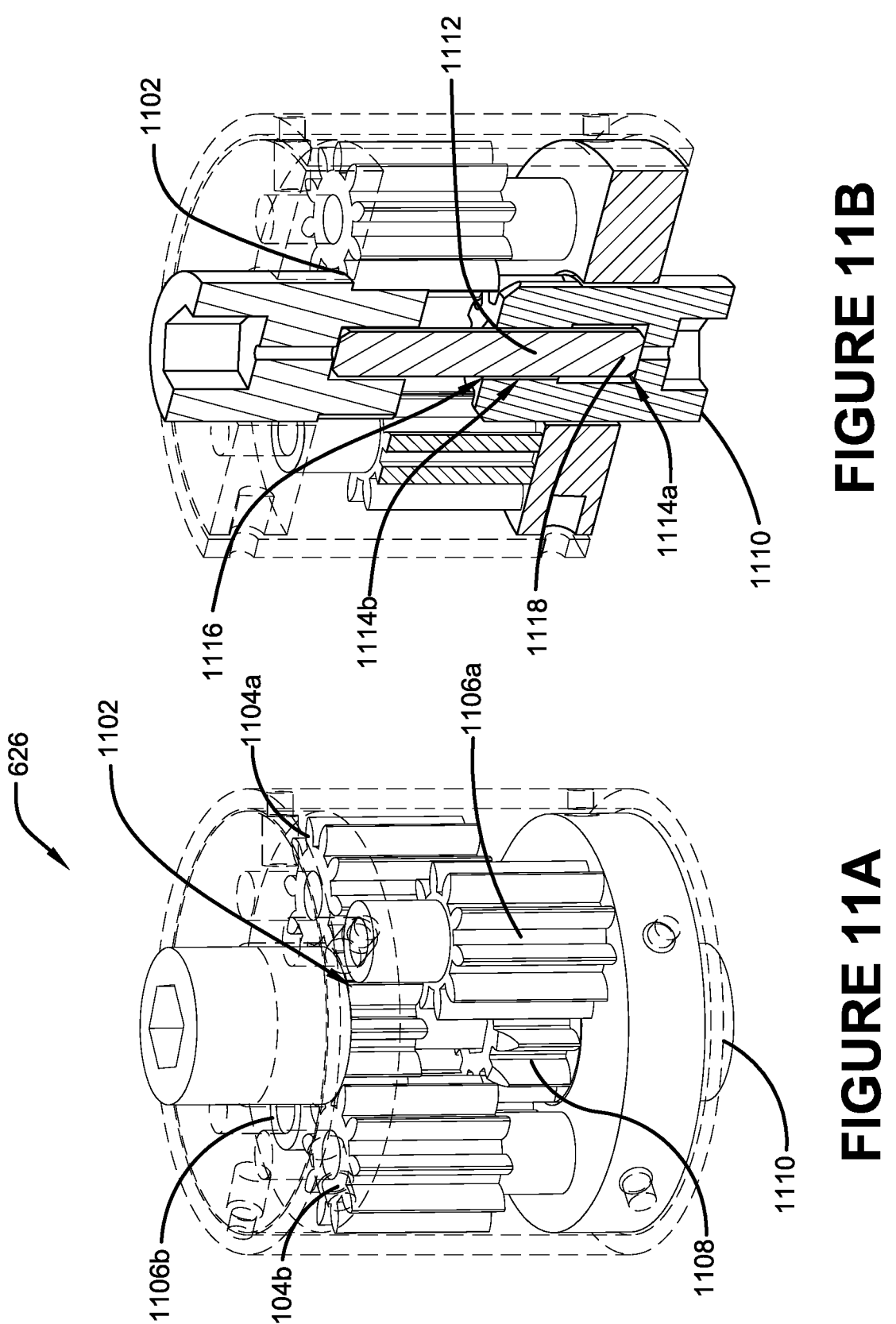
FIGS. 11A, 11B, 11C, and 11D are component diagrams illustrating an example implementation of one or more portions of systems and devices described herein, such as a component to change rotational direction of the output shaft.
Figures 11C, 11D:
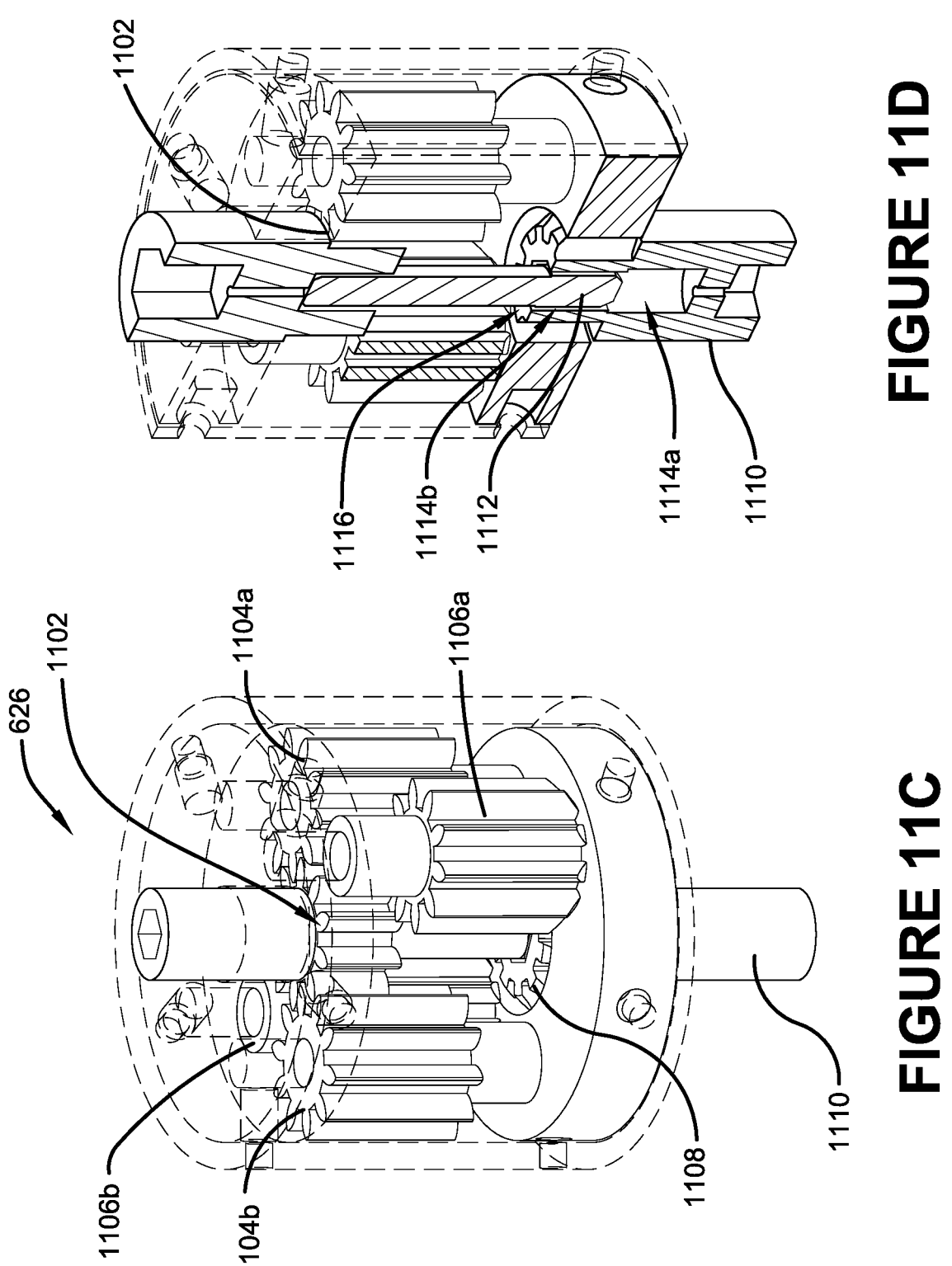

In some implementations, the example device 200 can comprise a rotation reversal mechanism 626 as shown in FIG. 11A, 11B, 11C, 11D. In this implementation, the rotation reversal mechanism 626 can comprises a input center gear 1102, which is driven by an input torque, two or more upper spur gears 1104a and 1104b, two or more lower spur gears 1106a and 1106b and a slidable center gear 1108 that can translate between an up and down position. The input center gear 1102 is meshedly engaged with the upper spur gears 1104a, 1104b, which are meshably engaged with the lower spur gears 1106a, 1106b. In some implementations the input center gear 1102 can comprise an extension 1112 with a medial cylindrical portion 1118a and a shaped end portion 1118b (e.g., a hex-drive extension), which is disposed inside a recess 1116 of the second drive shaft 1110. The recess has an annular inner recess 1114a disposed medially; and a shaped female feature 1114b at its end, which is complementary to the shaped end 1118b. As illustrated in FIGS. 11A and 11B, in an up position of the second drive shaft 1110 the second drive gear 1108 is meshably engaged with the lower spur gears 1106a and 1106b resulting in a reverse rotational direction of 1110 compared to 1102. In this example, the shaped portion 1118b of the extension 1112 of input center gear 1102 is disposed inside the medial annular inner recess 1114b of the second drive shaft 1110, which allows it to rotate freely without engaging with the second drive shaft 1110. Further, as illustrated in FIGS. 11C and 11D, with the second drive shaft 1110 (e.g., and center gear 1108) in a down position, the second gear drive 1108 is not meshably engaged with the lower spur gears 1106a and 1106b, but the shaped portion 1118b of the extension 1112 of the input center gear 1102 is disposed inside the complementary-shaped female feature 1114a of the second drive shaft 1110 resulting in engagement and transfer of force between driveshaft 1102 and driveshaft 1110, in a same rotational direction.

In some implementations, an example device can comprise a torque conversion mechanism (e.g., 628 of FIG. 6). FIGS. 8A-8H are component diagrams illustrating some example implementations of torque conversion mechanisms 802, 860, 862, which allows for selecting a torque output ratio with regard to torque input. As an example, the torque conversion mechanism 802 can comprise a planetary gear arrangement. For example, the purpose of this gear arrangement is to provide an input to output torque conversion, such as 1:1, 1:3, 1:4, etc. That is, in example 802, a ring gear 804 can be static, and a sun gear 806 can be driven with torque applied by the drive shaft 850 (e.g., connected to the driven pawl of the ratcheting mechanism 704b, 1006, or the secondary drive shaft of the rotation reversal mechanism 626). In this example, this results in planetary gears 808 orbiting the sun gear 806, providing rotation to a driver shaft 810. When engaged, for example, the torque output can comprise a 4-fold increase in torque, as illustrated in implementation 862 of FIGS. 8E-H with 4 planetary gears, or a 3-fold increase as illustrated in implementations 802, 860 of FIGS. 8A-D with three planetary gears (e.g., or some other ration depending on the number of teeth, size, and arrangement of gears).

In an alternate arrangement, as illustrated in FIGS. 8C-H, a bypass/switching option can be used, for example, to speed up initial tightening of the target fastener. That is, for example, the torque convertor 860, 862 can be switched between the 1:4 (e.g., or 1:3) torque input to output (e.g., which results in a slower rotation and 4-fold higher output torque of the driven shaft 810), to a 1:1 torque input to output, resulting in a faster rotation with the same output torque of the driven shaft 810. In this example, the example torque converter 860, 862 comprise a sun gear 812, planetary gears 814, a ring gear 804 or 820 (not shown in FIG. 8C, 8D), and a sliding shaft 812. In this implementation, a switch 852 can be engaged with a slidable sleeve 854 by attached pins 856. The sleeve 854 can be engaged with the central sun gear 812 to move it into and out of engagement with the planetary gears 814. When the sun gear 812 is disposed in engagement with the planetary gears 814, as in FIG. 8G, 8H, the 1:4 torque ratio is employed. In this example, when the sun gear 812 is disposed out of engagement with the planetary gears 814, as in FIG. 8E, 8F, the 1:1 torque ratio is employed, because the male drive 816 directly engages the female feature 818. Further, the torque ratio may be adjust using different arrangements, numbers, and dimensions of torque converter components.

In one implementation, an example device (e.g., 200) can comprise a torque limiter (e.g., 630 of FIG. 6). For example, as illustrated in FIG. 9, a torque limiter 902 can be configured to provide a predetermined output of torque, which can be limited to desired torque value. As an example, the torque limiter 902 can comprise a "ring-spring" torque limiter, which is operable for a predetermined amount of torque, and precision machined ring-spring 910 with a tab 904, which is operably disposed in a groove 906 of a central drive shaft engagement sleeve 908. In one example, the ring-spring 910 can be machined in such a way as part of the housing 912 where a predetermined amount of torque is utilized to rotate the tab 904 out of the groove 906. As an example, when the amount of torque applied to the drive shaft, and hence the shaft sleeve 908, the torque will be transferred from groove 906 to tab 904 and thereby to the output shaft (not shown), which is rigidly connected to the housing 912. If the torque transfer exceeds the predetermined allowable torque transfer value between tab 904 and groove 906, then the tab 904 will translate out of groove 906 (e.g., producing an audible "click"), which indicates the preselected amount of torque has been reached. In this example, because the tab 904 is no longer disposed inside the groove 906, no additional torque will be transferred. It is anticipated that other suitable torque limiting mechanisms are also contemplated for use in the device. For example, the use of an electro-mechanical torque limiter is anticipated for devices using an electric motor as a power source. In those implementations the current draw by the electrical motor can be monitored in order to turn off the motor, when the current draw has reached a value that correspond to a predetermined torque level.

Figure 12:
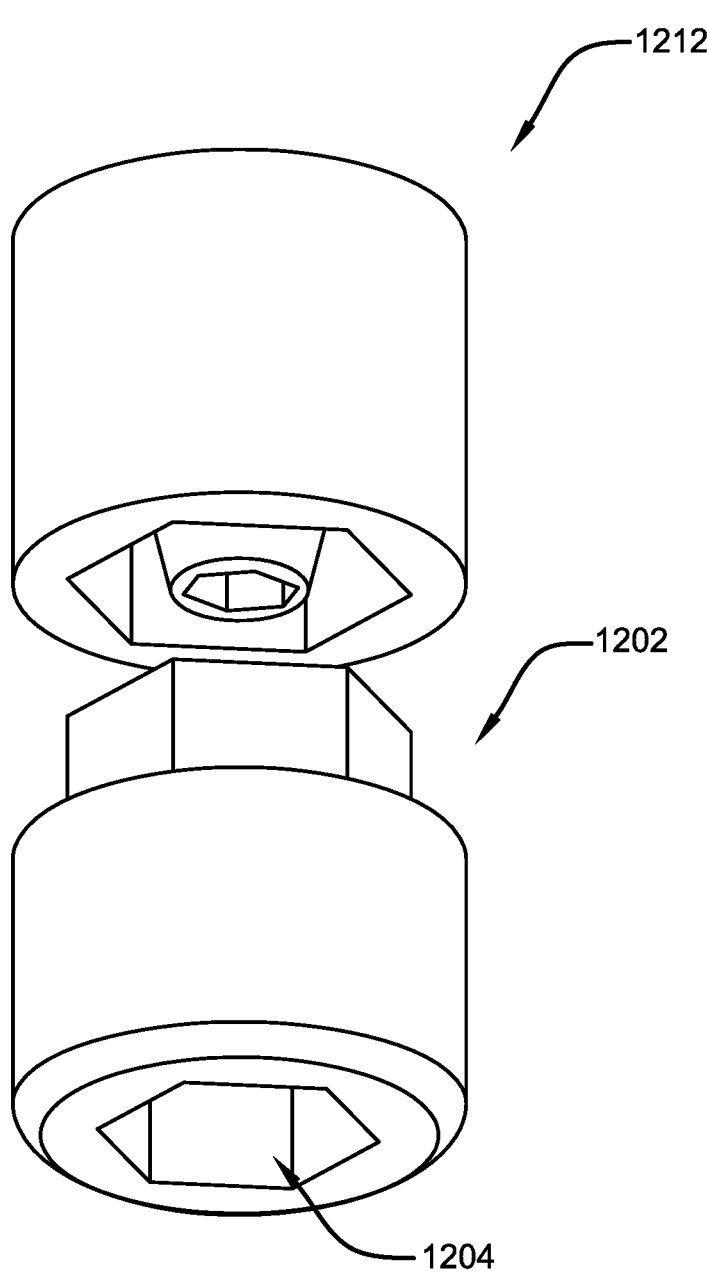
FIG. 12 is a component diagram illustrating an example implementation of one or more portions of systems and devices described herein, such as a driver head holder.
Figures 13, 14:
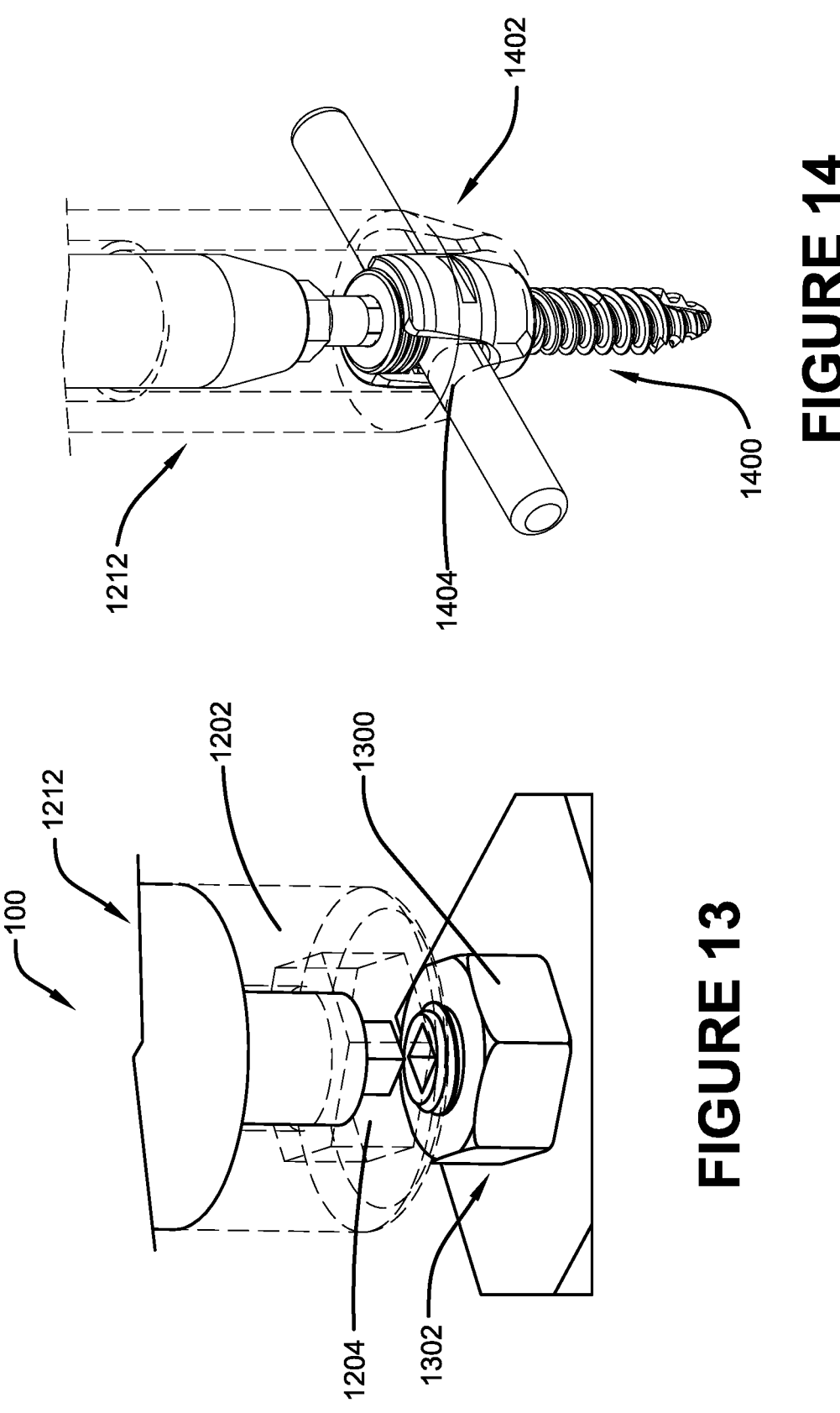
FIG. 13 is a component diagram illustrating an example implementation of one or more portions of systems and devices described herein, such as another driver head holder.
FIG. 14 is a component diagram illustrating an example where one or more portions of systems and devices described herein may be implemented, such as to drive a threaded fastener.
Figures 15A, 15B:
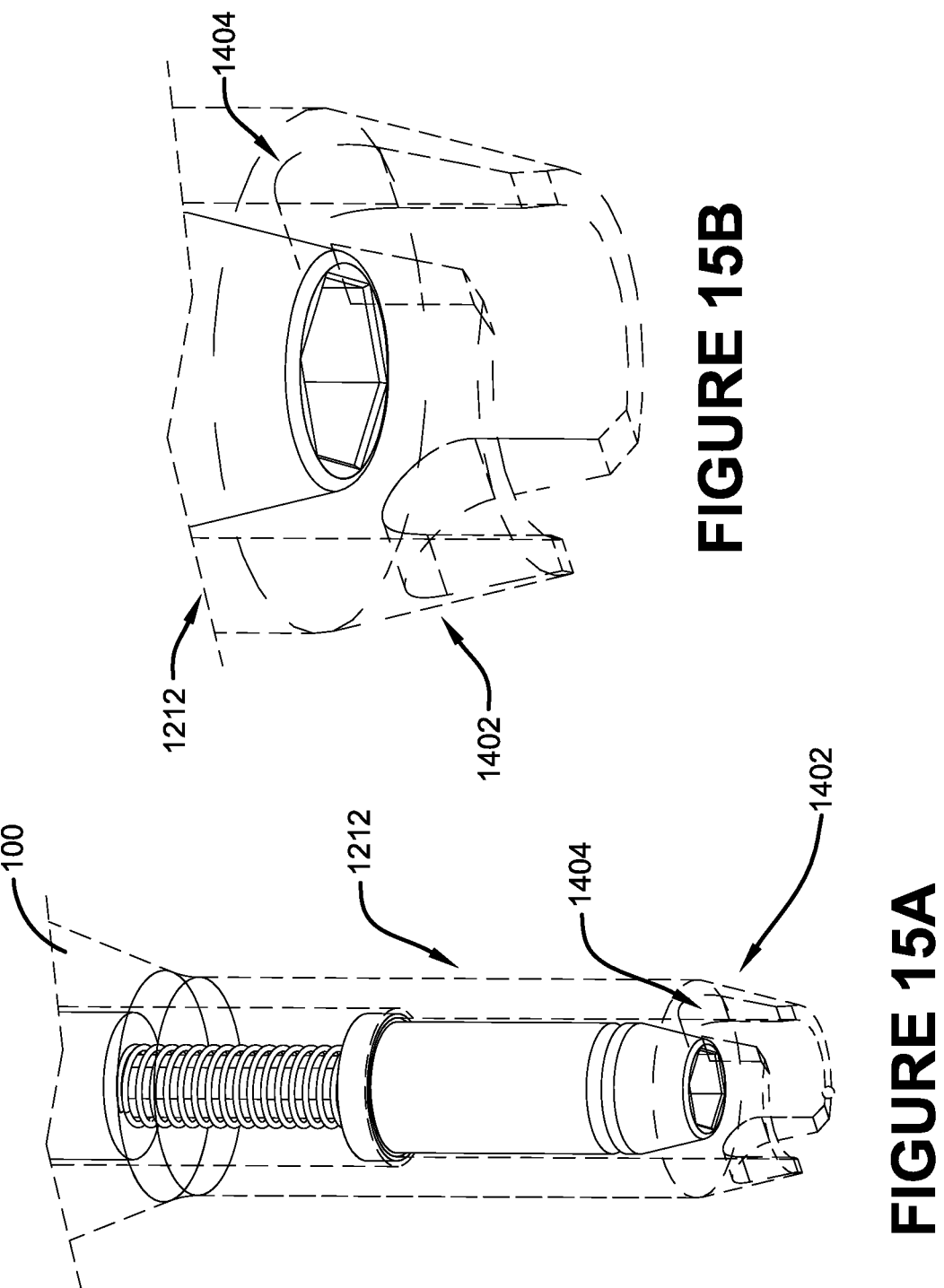
FIGS. 15A and 15B are component diagram illustrating one example implementation of one or more portions of the one or more systems and devices described herein.

As illustrated in FIG. 12, a counter-torque component 1202 (e.g., tool tip) can be selectably engaged (e.g., selectably fixed and removed/replaced) with the counter-torque component holder portion 1212 (e.g., 212) of an example device. As an example, as illustrated in FIGS. 13, 14, 15A, and 15B, a target base 1300, 1400 (e.g., into which a target fastener is driven and/or removed) can comprise a variety of shapes and sizes. In this implementation, a counter-torque tool 1202, 1402 (e.g., the component formed to engage the target base) can be configured to engage/fit the target base 1300, 1400. As illustrated, for example, counter-torque tool 1202 has a hex-shaped cavity 1204 that is configured to operably fit over the hex-shaped protrusion (e.g., nut) of the target base 1300. Further, for example, the counter-torque tool 1402 has a slot-shaped cavity 1404 that is configured to operably fit over the bar portion of the target base 1400 (e.g., a spinal stabilization bar). In this way, for example, the appropriate counter-torque tool can be fixedly engaged with the counter-torque component holder portion of the device and hold the device stationary with respect to the target base, while a fastener is driven into, and fixed to, the target base. It is anticipated that various shapes, sizes and configuration of counter-torque sleeves can be design depending on the configuration of the target component.

Figure 16B:
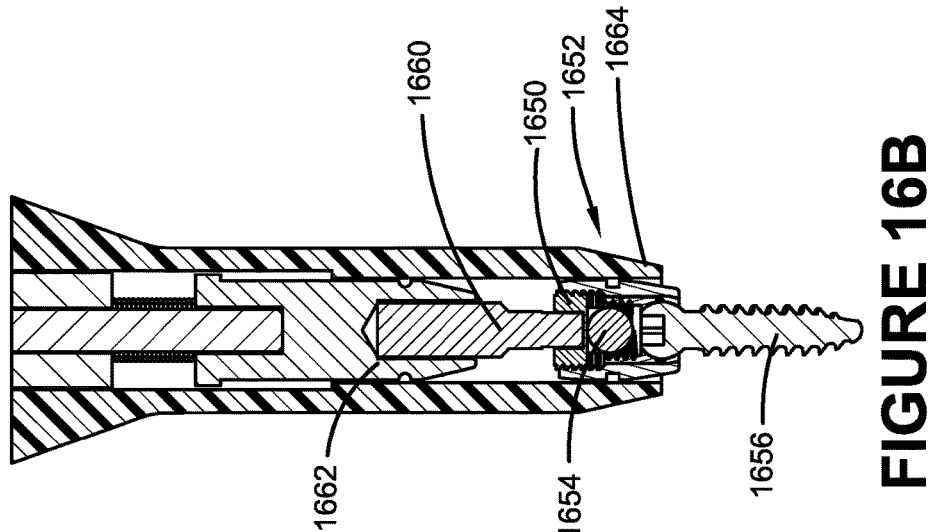
FIGS. 16A and 16B are component diagram illustrating another example implementation of one or more portions of the one or more systems and devices described herein.
Figure 16A:
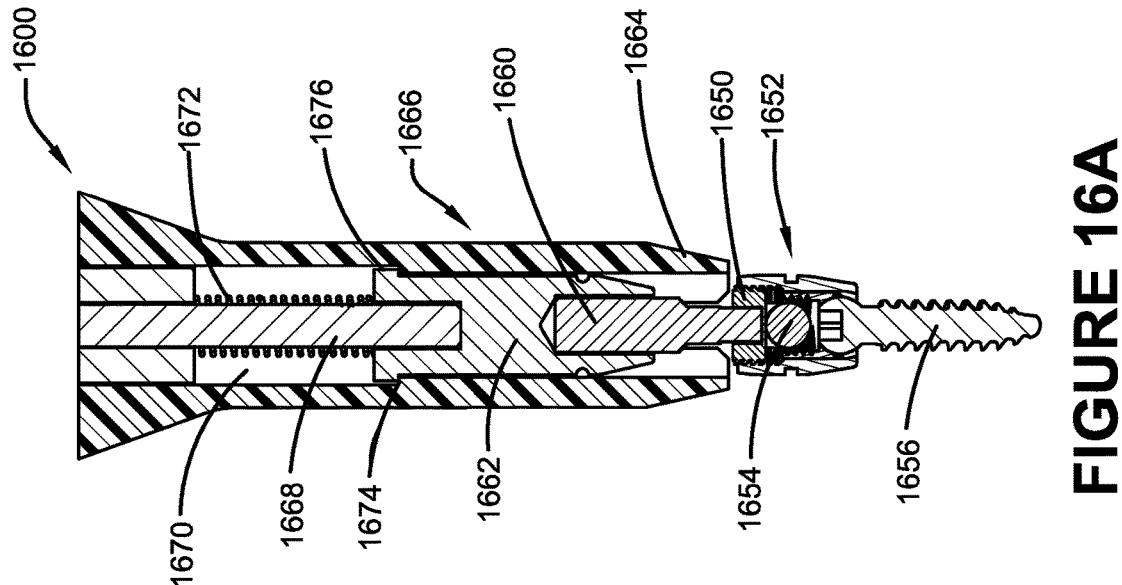

FIGS. 16A and 16B are component diagrams illustrating an example implementation of a portion of an example device 1600, where a target fastener 1650 (e.g., a set screw) is operably engaged with a target base 1652 (e.g., a spinal stabilization apparatus). In this example, the target fastener 1650 can comprise a set screw that can be operably tightened or loosened into the target base 1652, which is used to secure a spinal stabilization rod 1654 to a pedicle screw 1656. As illustrated, a selectably removable fastener bit tool 1660 can be chosen to operably accommodate the head of the fastener 1650. The bit tool 1660 is engaged into the bit holder 1662 of the device. An appropriate counter-torque tool 1664 is selected and fixedly engaged onto the end of the counter-torque component holder portion 1666. In this example, the counter-torque tool 1664 can be selected with a slot-shaped groove or cavity to operably fit over the stabilization rod 1654. As illustrated, the fastener bit tool 1660 is operably engaged with the fastener 1650 in FIG. 16A. In FIG. 16B, the counter-torque tool 1664 can be operably fit over the target base 1652, in this case the stabilization rod 1654 portion. In other implementations, the counter-torque tool 1664 can be configured to operably fit over a different target base, such as the housing of a pedicle screw system.

In this implementation, the example device 1600 comprises a bit holder 1662 and driven rotating shaft 1668, that can translates up and down inside a cavity 1670 in the counter-torque component holder portion 1666. Further, a biasing spring 1672 is disposed inside the cavity 1670 to provide a biasing force against the bit holder 1662, toward the distal end of the device 1600. In this way, the biasing force drives the bit holder 1662 toward the distal end (e.g., second end). A bit holder stop 1674 is disposed at the distal end of the cavity 1670 to engage with a shoulder 1676 on the bit holder 1662. In this way, for example, the biasing force will provide for the removable fastener bit initially protruding from the counter-torque sleeve 1664 for easier insertion of the fastener bit tool 1660 into the fastener, while holder stop 1674 stops the bit holder 1662 from being pushed out of the counter-torque tool 1664.

Figures 17A, 17B:
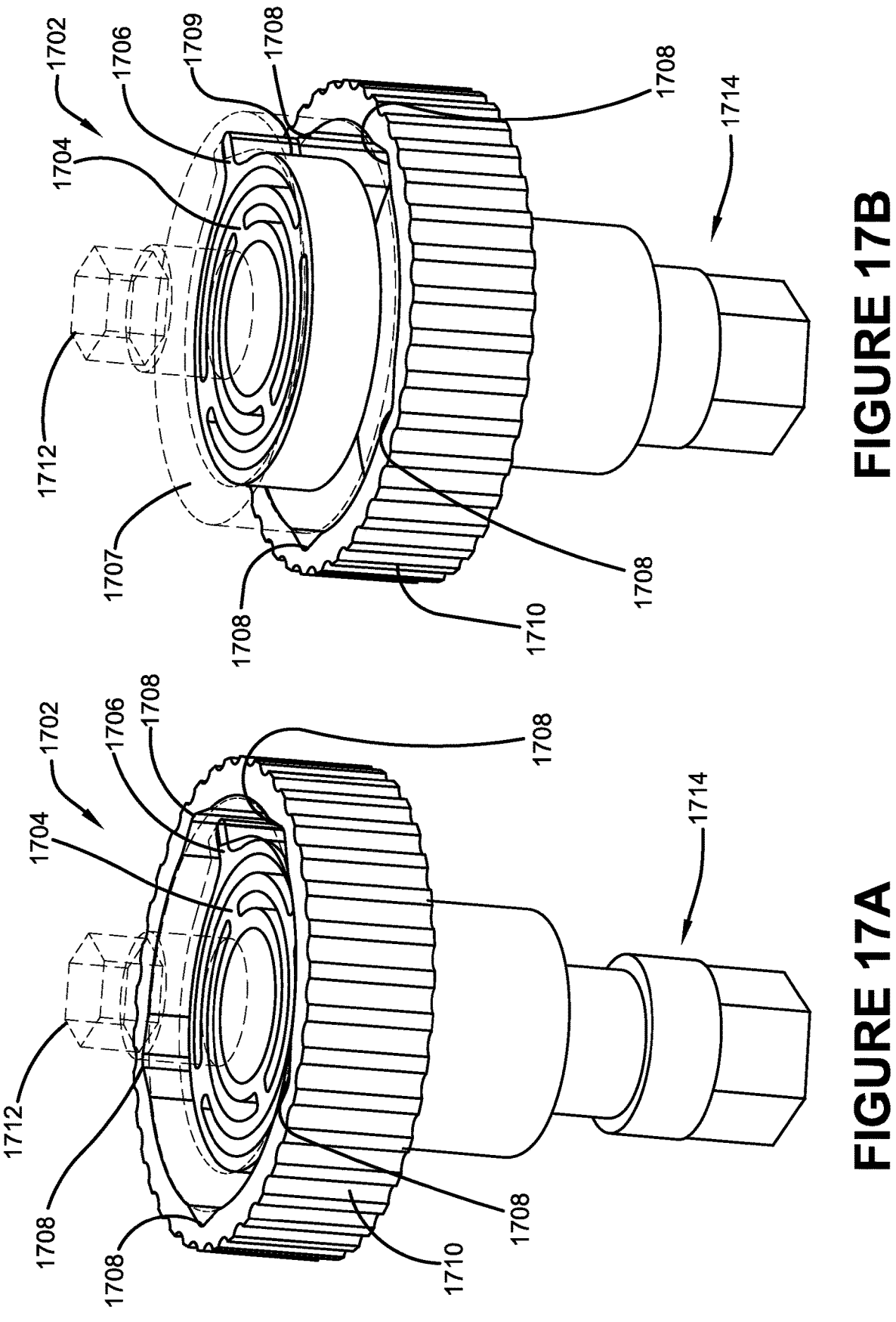
FIGS. 17A, 17B, and 17C are component diagram illustrating an example implementation of one or more portions of the one or more systems described herein, such as a torque limiter with variable values of torque.

FIGS. 17A and 17B illustrate another example implementation of a torque limiter (e.g., FIG. 9). As illustrated in FIG. 17A, a torque limiter 1702 can be configured to provide a predetermined limit of torque output (e.g., optionally preselected), which can be preselected at different desired torque values. As an example, the torque limiter 1702 can comprise a drive shaft 1712, a housing 1707 for a predetermined (e.g., amount of torque), and precision machined ring-spring 1704. An integrated pin 1706 can be operably disposed inside a groove 1709 of housing 1707 and protrude into a recess 1708 of an outer ring 1710. In this implementation, one or more recesses 1708 (in this example five) can be disposed in the outer ring 1710, each having a different sized/shaped cavity (e.g., with different depths, wall angles, etc.), thereby creating different tangential forces to discharge the pin 1706 at a predetermined torque.

As an example, the biasing force of the ring-spring 1704 is substantially constant (e.g., predetermined by design, illustrated below in FIG. 18), and the recesses 1708 each have different shapes/sizes designed for different torque values. In this example, the pin 1706 is operably disposed into a pre-selected recess. Thus, the torque value that results in the pin 1706 discharging out of the selected recess 1708 is determined by the different depths and wall angles of a recess 1708, and the associated tangential force. As an example, when torque is applied to the drive shaft 1712, and hence to the housing 1707, the torque will be transferred from the housing 1707 to the pin 1706 and then from the pin 1706 to the selected recess 1708, and thereby to the outer ring 1710. The outer ring 1710 is rigidly connected in rotation to the output shaft 1714. Therefore, in this example, if the torque transfer is below the predetermined threshold torque transfer value between the pin 1706 to the selected recess 1708, then the outer ring 1710 and output shaft 1714 will rotate with the same input torque as drive shaft 1712. Further, when the torque transfer exceeds the predetermined threshold torque transfer value between the pin 1706 to the selected recess 1708, the pin 1706 will dislodge from the selected recess 1708 and subsequent rotation is mitigated, at least until reset. In this example, the dislodging of the pin 1706 can produce an audible "click," which indicates to the user that the preselected amount of torque has been reached. Further, because the pin 1706 is no longer seated inside the selected recess 1708, torque is no longer be transferred. It is anticipated that other suitable torque limiting mechanisms are also contemplated for use in the device.

As illustrated in FIG. 17B, as an example, when selecting the appropriate recess 1708 in the outer ring 1710 for the position of the pin 1706 (e.g., and thus pre-selected torque value), the outer ring 1710 may be axially pushed down, which disengages the pin 1706 from the outer ring 1710, and the outer ring 1710 from the output shaft 1714. In this example, the outer ring 1710 can be rotated to another selected recess 1708 and released, such that the outer ring 1710 is axially spring loaded upward. In this example, the resulting new engagement between pin 1706 and the newly selected recess 1708 can create a rotational engagement between outer ring 1710 and output shaft 1714. As an example, in FIG. 17C, a top view of torque limiter 1702 illustrates a ring-spring 1704 with an integrated pin 1706, which is inserted through a groove 1709 of housing 1707 and further protrudes into a recess 1708 of an outer ring 1710.

Figure 17C:
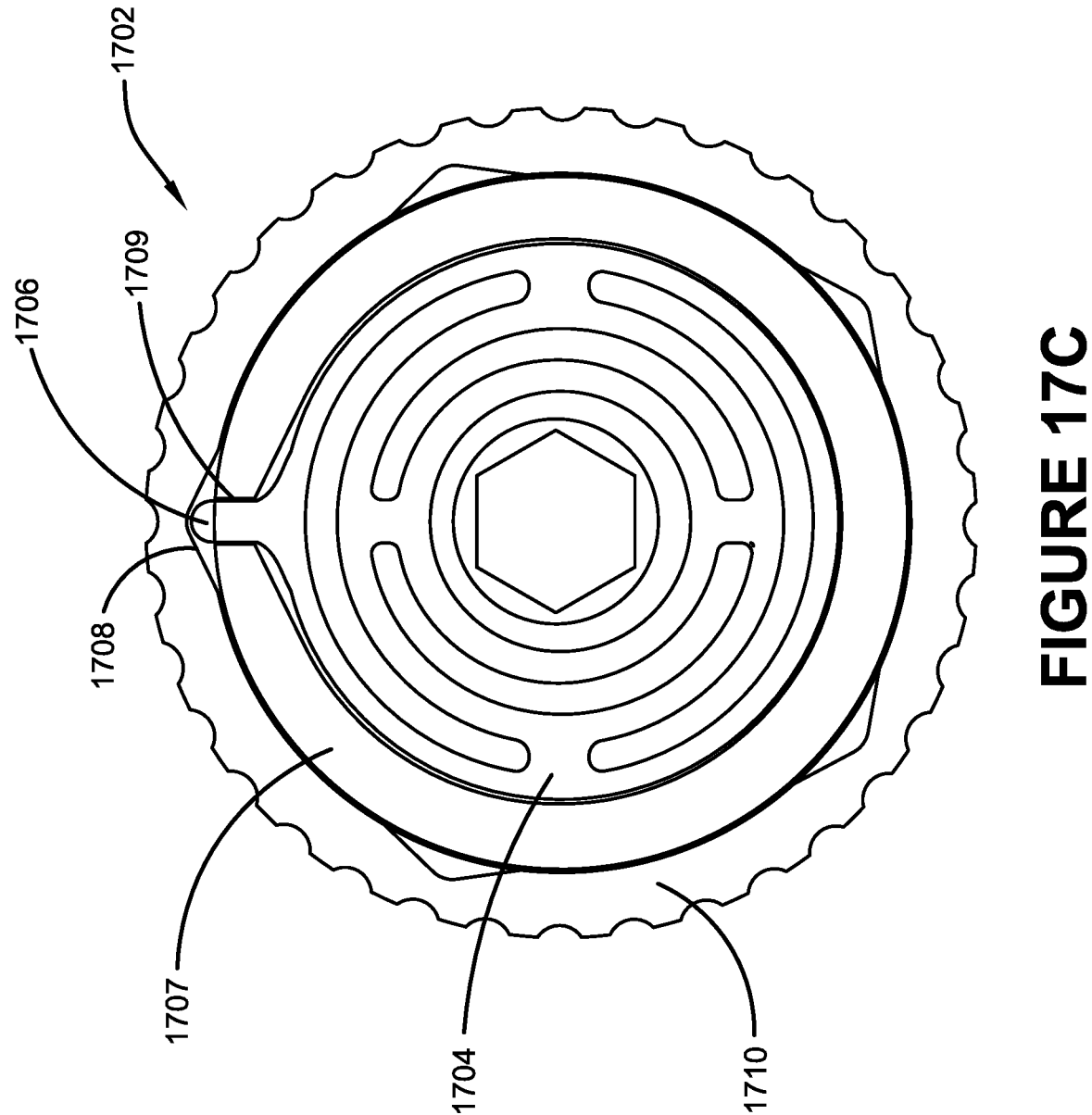
Figures 18A, 18B, 18C, 18D:
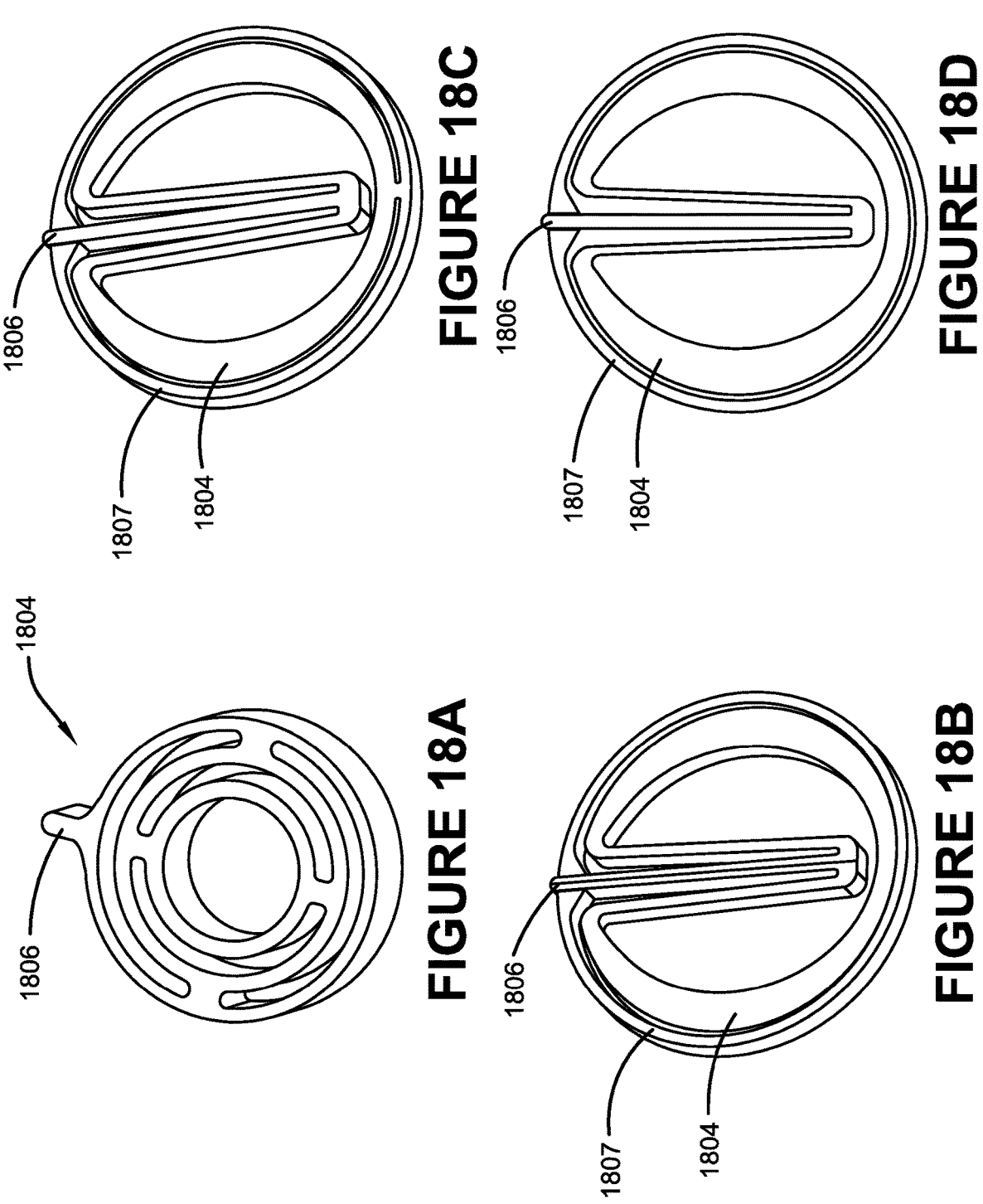
FIGS. 18A, 18B, 18C, 18D, 18E, 18F, and 18G are component diagram illustrating an example implementation of one or more portions of the one of more systems described herein, such as torque limiter spring.
Figures 18E, 18F, 18G:
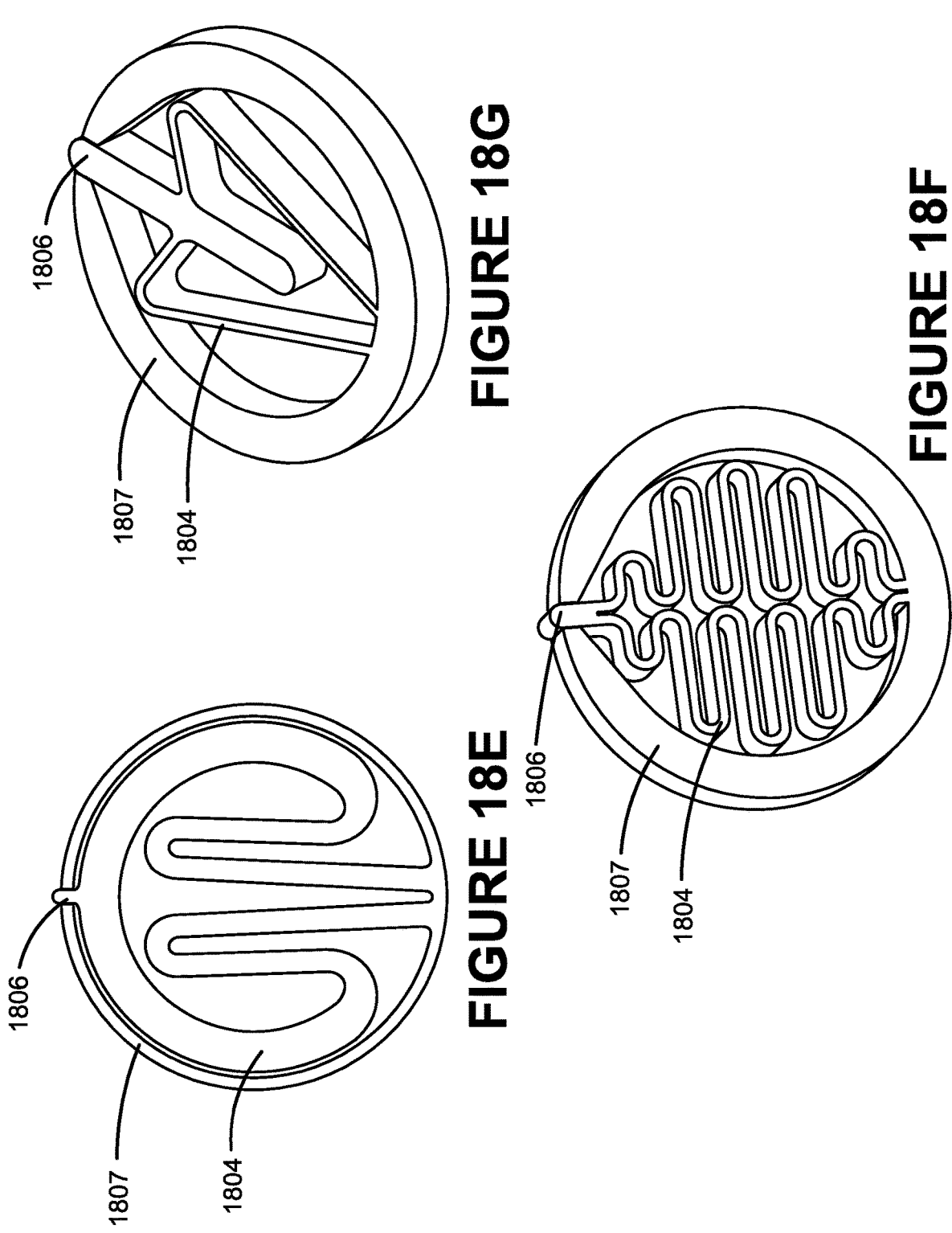

In other implementations of a ring-spring (e.g., 1704 in FIGS. 17A, 17B, 17C), for example, as illustrated in FIG. 18A, a ring-spring has a predetermined (e.g., threshold amount of torque) and precision machined ring-spring 1804 with pin 1806 either integrated or seated inside a housing 1807. Also as illustrated in FIGS. 18B, 18C, 18D, 18E, 18F, and 18G, there are multiple varied configurations of the ring-spring 1804, each machined with a predetermined amount of torque and a pin 1806 configured to engage a recess (not shown). Those skilled in the art would appreciate these and other suitable ring-spring configurations. In other implementations, for an electro-mechanical torque limiter, an operator can define a desired torque limit, for example, with a dial, digital input, touchscreen input, etc., which thereby defines a predetermined set-point for the current draw that can trigger the motor to shut off.

Figure 19B:
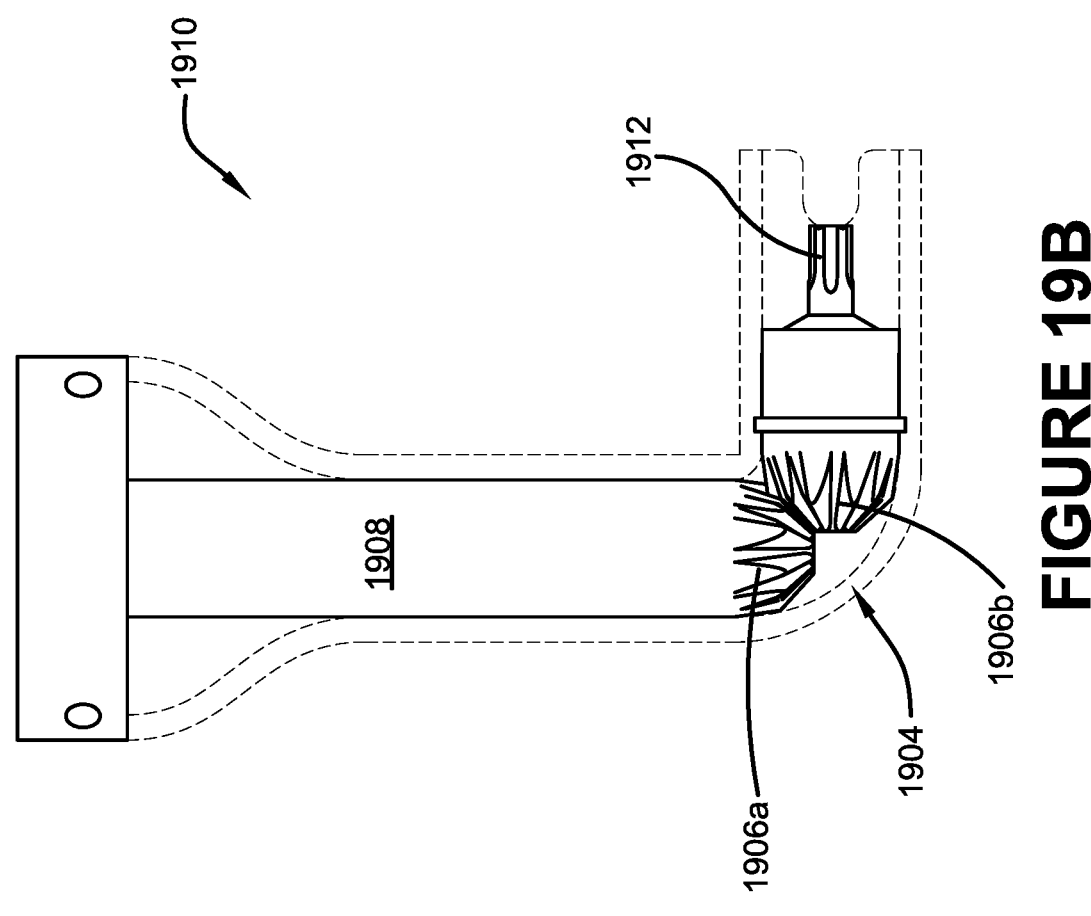
FIGS. 19A, 19B, 19C, 19D, 19E, 19F, 19G, and 19H are component diagram illustrating an example implementation of one or more portions of the one of more systems described herein, such as an angled driver and/or a stationary driver shaft with a rotational outer tube.
Figure 19A:
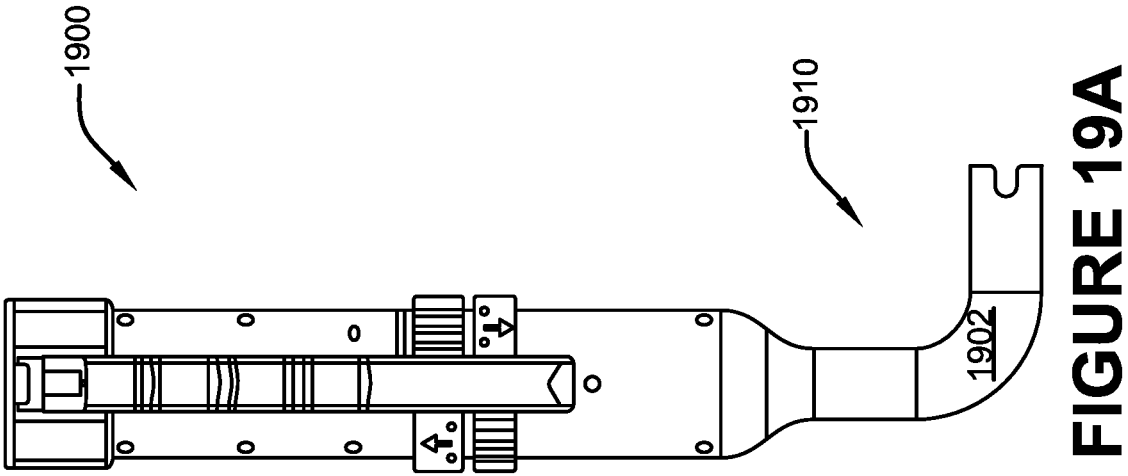

In FIGS. 19A, 19B, 19C, 19D, 19E, 19F, 19G, and 19H are component diagrams illustrating an example implementation of a portion of an example device 1900, namely an angled shaft 1910, comprised of a cover 1902 and rotating inner shaft components 1904. The example device 1900 may be powered manually, by electric motor, pneumatic drive, hydraulic drive, or any other suitable means. The diagram angles are shown as 90 degrees, but it is contemplated that it may be configured to any suitable angle. As illustrated in FIG. 19A, an implementation of the angled shaft 1910 may include a cover 1902 that contain the rotating inner shaft components 1904. As shown in FIG. 19B the rotating inner shaft components 1904 comprise a pair of bevel gears 1906a, 1906b. As illustrated in this implementation, the bevel gears 1906a and 1906b are meshedly engaged at a 90-degree angle, however it is appreciated that the bevel gears 1906a and 1906b may be machined to engage at any suitable angle. As output shaft 1908 rotates clockwise or counterclockwise so does bevel gear 1906a, as it is fixedly attached to output shaft 1908. As bevel gear 1906a rotates, bevel gear 1906b rotates in the same direction thus rotating the fastener driving portion 1912 also in the same direction.

Figures 19C, 19D:
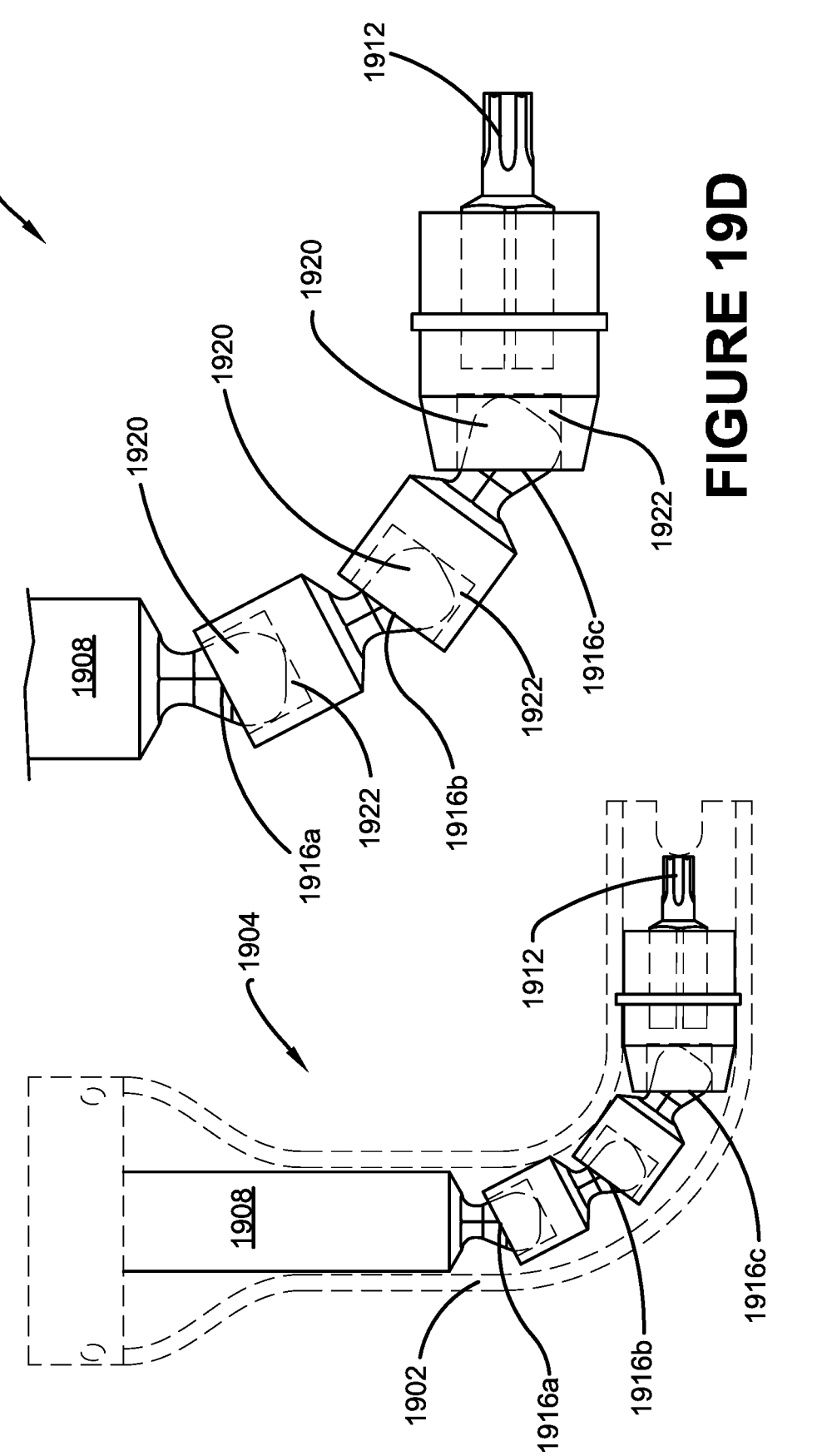

FIGS. 19C and 19D illustrate alternate implementation of a device that applies torque and counter-torque. In these implementations, an angled driver 1910 may include a cover 1902 (not shown in 19D), where the rotating inner shaft components 1904 are at least two (three are shown) round-ball-hex joints 1916a, 1916b, and 1916c. Each round-ball-hex joint 1916a, 1916b, and 1916c comprises a spherical-like hex-ball 1920 and a hexagonal socket 1922, where each hex-ball 1920 is disposed into its associated hexagonal socket 1922. Each hex-ball 1920 is made up of small flat planes that create the spherical-like shape, when disposed into the hexagonal socket 1922 some of the small flat planes fully contact the inner surface of the hexagonal socket 1922 such that torque applied the hex-ball 1920 directly transfers to the hexagonal socket 1922. The hex-ball 1920 of round-ball-hex joint 1916a is fixedly attached to the output shaft 1908, such that torque applied to the output shaft 1908 transfers to the hex-ball 1920 of round-ball-hex joint 1916a.

Thus, in this example, torque applied to the hex-ball 1920 of round-ball-hex joint 1916a, transfers to the hexagonal socket 1922 of round-ball-hex joint 1916a. The hexagonal socket 1922 of round-ball-hex joint 1916a is fixedly attached to the ball 1920 of round-ball-hex joint 1916b. Thus, torque applied to the ball 1920 of round-ball-hex joint 1916b, transfers to the hexagonal socket 1922 of round-ball-hex joint 1916b. The hexagonal socket 1922 of round-ball-hex joint 1916b is fixedly attached to the ball 1920 of round-ball-hex joint 1916c. Thus, torque applied to the hex-ball 1920 of round-ball-hex joint 1916c, transfers to the hexagonal socket 1922 of round-ball-hex joint 1916c. The hexagonal socket 1922 of round-ball-hex joint 1916c is fixedly attached to the bit 1912. The angles in the diagrams are shown as 90 degrees, but it is contemplated that it may be configured to any suitable angle. It may be appreciated that cover 1902 (not shown) is made of an appropriate flexible material containing the round-ball-hex joints 1916a, 1916b, and 1916c that are flexible thereby the angled driver 1910 has an impermanent flexible angle.

Figures 19E, 19F:
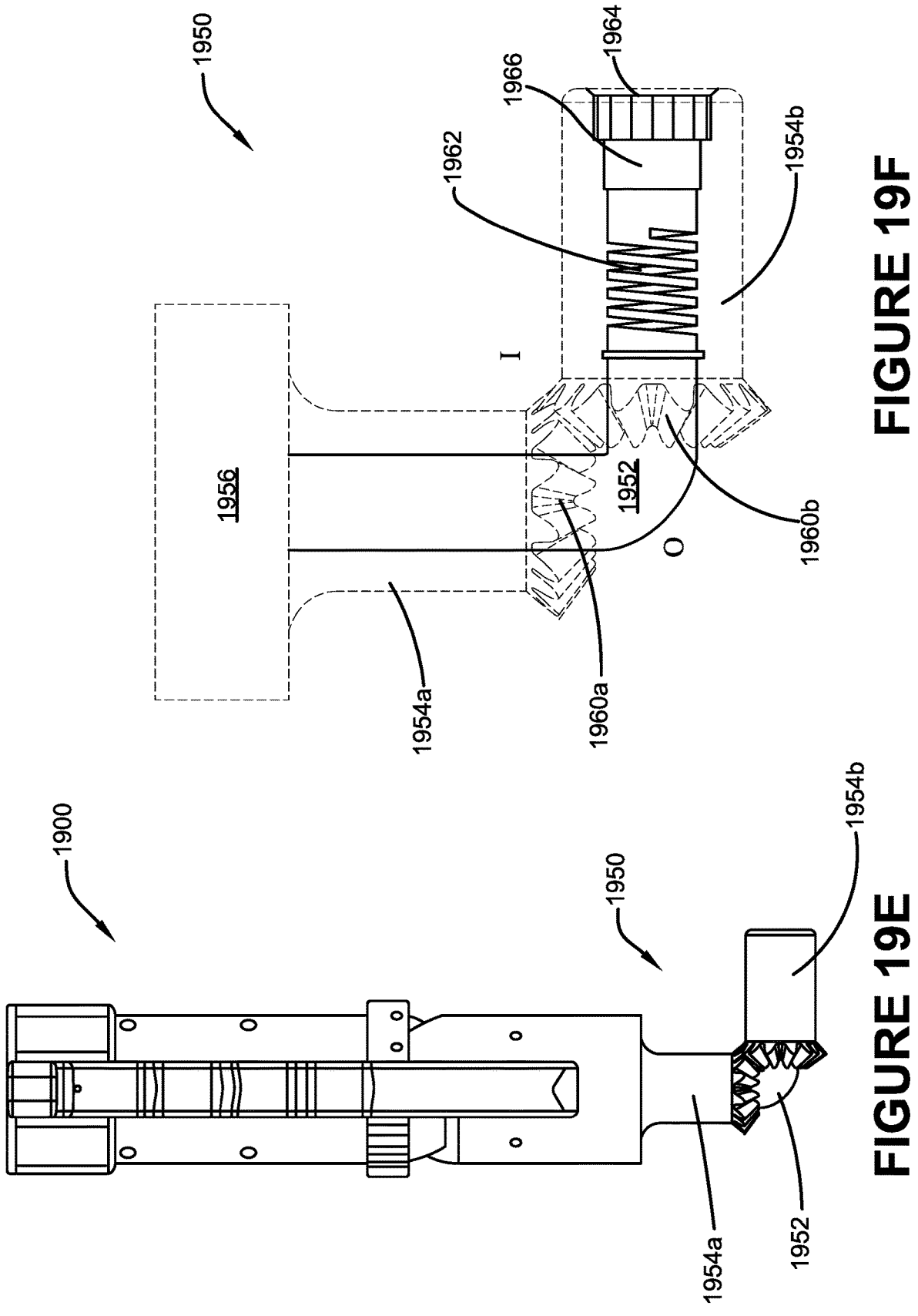

In another implementation, an example device 1900 is illustrated in FIGS. 19E, 19F, 19G, and 19H. An angled driver 1950 comprises an operably, stationary inner shaft 1952 and a rotating outer shaft 1954a and 1954b (e.g., tube). In this example, the arrangement allows for an example nut and bolt-type fastening arrangement (described in detail below with FIG. 21). As an example, as shown in FIGS. 19E and 19F, the angle driver 1950 comprises an inner (non-rotating) shaft 1952, an outer rotating shaft 1954a and 1954b (e.g., tube) with a pair of bevel gears 1960a and 1960b respectively. In this implementation outer rotating shaft 1954a is fixedly attached to output shaft 1956 and contains a first portion of stationary inner shaft 1952. Outer rotating shaft 1954b has a nut receiver 1964 and contains a second portion of stationary inner shaft 1952 that is a spring 1962. The distal end of the spring 1962 has a bolt receiver 1966.

The stationary inner shaft 1952 is disposed through the outer rotating shaft 1954a and 1954b such that the stationary inner shaft 1952 is disposed at an angle (shown as 90 degrees in this implementation). The stationary inner shaft 1952 bend has an inner corner I and an outer corner O, where the pair of bevel gears 1960a and 1960b meshedly engage at inner corner I. It is appreciated that the stationary inner shaft 1952 and bevel gears 1960*a* and 1960*b* may be machined to be disposed through and engage at any suitable angle. In this implementation, as the output shaft 1956 rotates, so does the outer rotating tube 1954*a* and bevel gear 1960*a*. As bevel gear 1960*a* rotates it meshedly engages bevel gear 1960*b* to rotate in the same direction thus also rotating the outer rotating shaft 1954*b* and the nut receiver 1964 in that same direction. As the example device 1900 is powered by suitable means, the outer rotating tube 1954*b* rotates as described above and thereby the nut receiver 1964 applies torque to a target fastener (not shown), while the distal end 1966 of the spring 1962 applies a counter torque to a target component, such as 2126 in FIG. 21C.

Figures 19G, 19H:
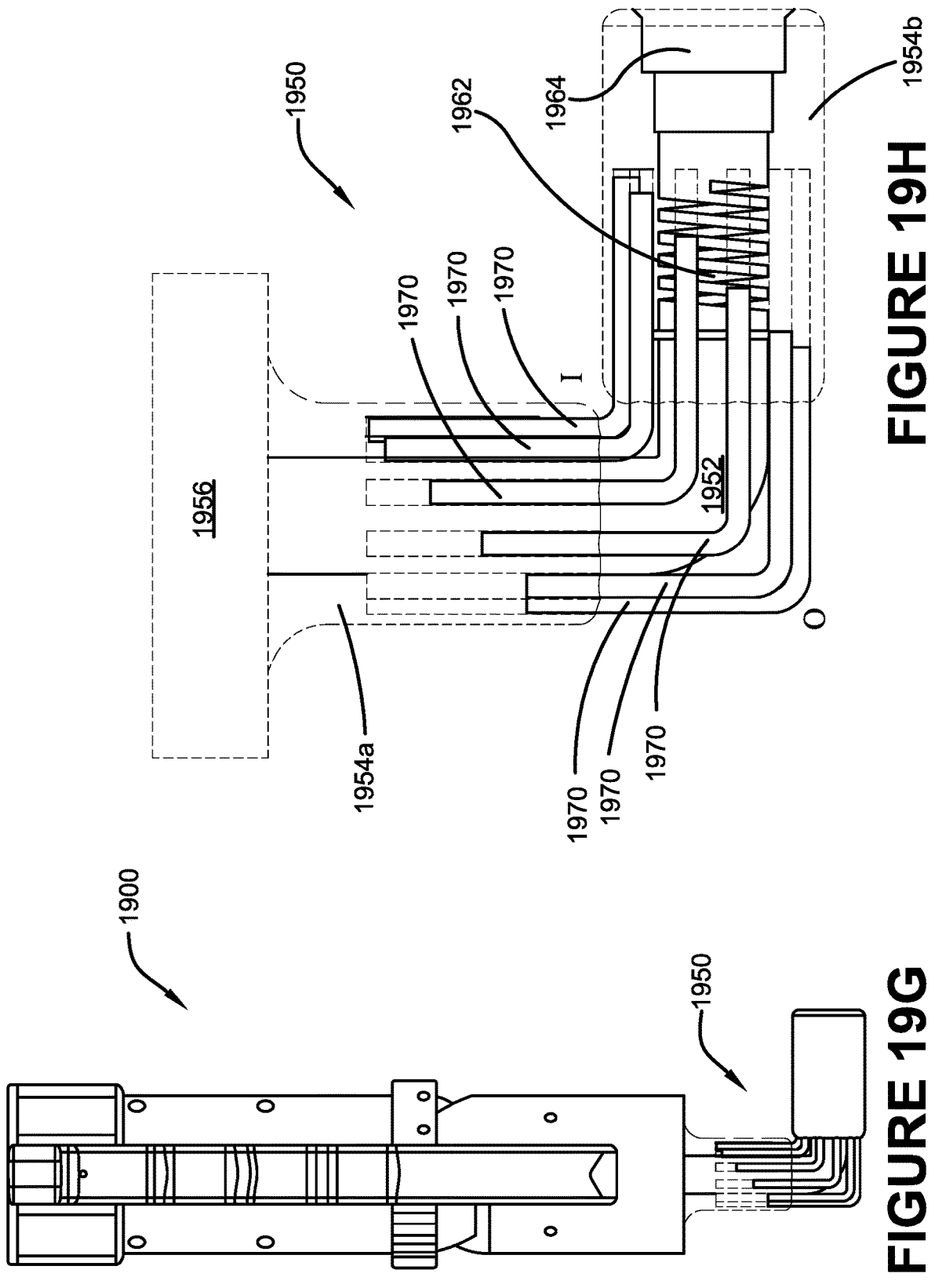

An example is shown in FIGS. 19G and 19H, the angle driver 1950 comprises an inner (non-rotating) shaft 1952, an outer rotating shaft 1954*a* and 1954*b* (e.g., tube) with a plurality of slidable rods 1970 where respective slidable rods are substantially uniform in size. In this implementation outer rotating shaft 1954*a* is fixedly attached to output shaft 1956 and contains a first portion of stationary inner shaft 1952. Outer rotating shaft 1954*b* has a nut receiver 1964, contains a second portion of stationary inner shaft 1952 that is a spring 1962. The distal end of the spring 1962 has a bolt receiver 1966. The stationary inner shaft 1952 is disposed through the outer rotating shaft 1954*a* and 1954*b* such that the stationary inner shaft 1952 is disposed at an angle (shown as 90 degrees in this implementation) where the plurality of slidable rods 1970 are also disposed at a similar angle.

The stationary inner shaft 1952 bend has an inner corner I and an outer corner O. It is appreciated that the stationary inner shaft 1952 and plurality of slidable rods 1970 may be machined to be disposed through and bent at any suitable angle. The plurality of slidable rods 1970 are slidably inserted circumferentially within the walls of the outer rotating shaft 1954*a* and 1954*b*, such that the slidable rods nearest inner corner I are fully inserted into the walls of the outer rotating shaft 1954*a* and 1954*b*, and the slidable rods nearest the outer corner O are at least partially inserted into the walls of the outer rotating shaft 1954*a* and 1954*b*. The amount of insertion of the slidable rods inserted between inner corner I and outer corner O is gradually increased or decreased as the outer rotating tube 1954*a* and 1954*b* rotate. As the outer rotating shaft 1954*a* and 1954*b* rotate, the insertion of the slidable rods rotating in the direction of inner corner I to outer corner O is decreased. Likewise, as the outer rotating tube 1954*a* and 1954*b* rotate, the insertion of the slidable rods rotating in the direction of outer corner O to inner corner I is increased.

In this implementation, as the output shaft 1956 rotates clockwise as does outer rotating tube 1954*a* and the plurality of slidable rods 1970. As the plurality of slidable rods 1970 rotate clockwise they rotate the outer rotating shaft 1954*b* clockwise and the nut receiver 1964. Likewise, rotation of the output shaft 1956 in a counterclockwise direction also rotates the outer rotating shaft 1954*a* in a same direction, along with the plurality of slidable rods 1970. As the plurality of slidable rods 1970 rotate counterclockwise the outer rotating tube 1954*b* can rotate in a counterclockwise direction, along with the nut receiver 1964. As the example device 1900 is powered by suitable means, the nut receiver 1964 applies torque to a target fastener (not shown), while the distal end 1966 of the spring 1962 applies a counter torque to a target component, such as 2126 in FIG. 21C. The angle in the diagram is shown as 90 degrees, but it is contemplated that it may be configured to any suitable angle.

Figures 20A, 20B:
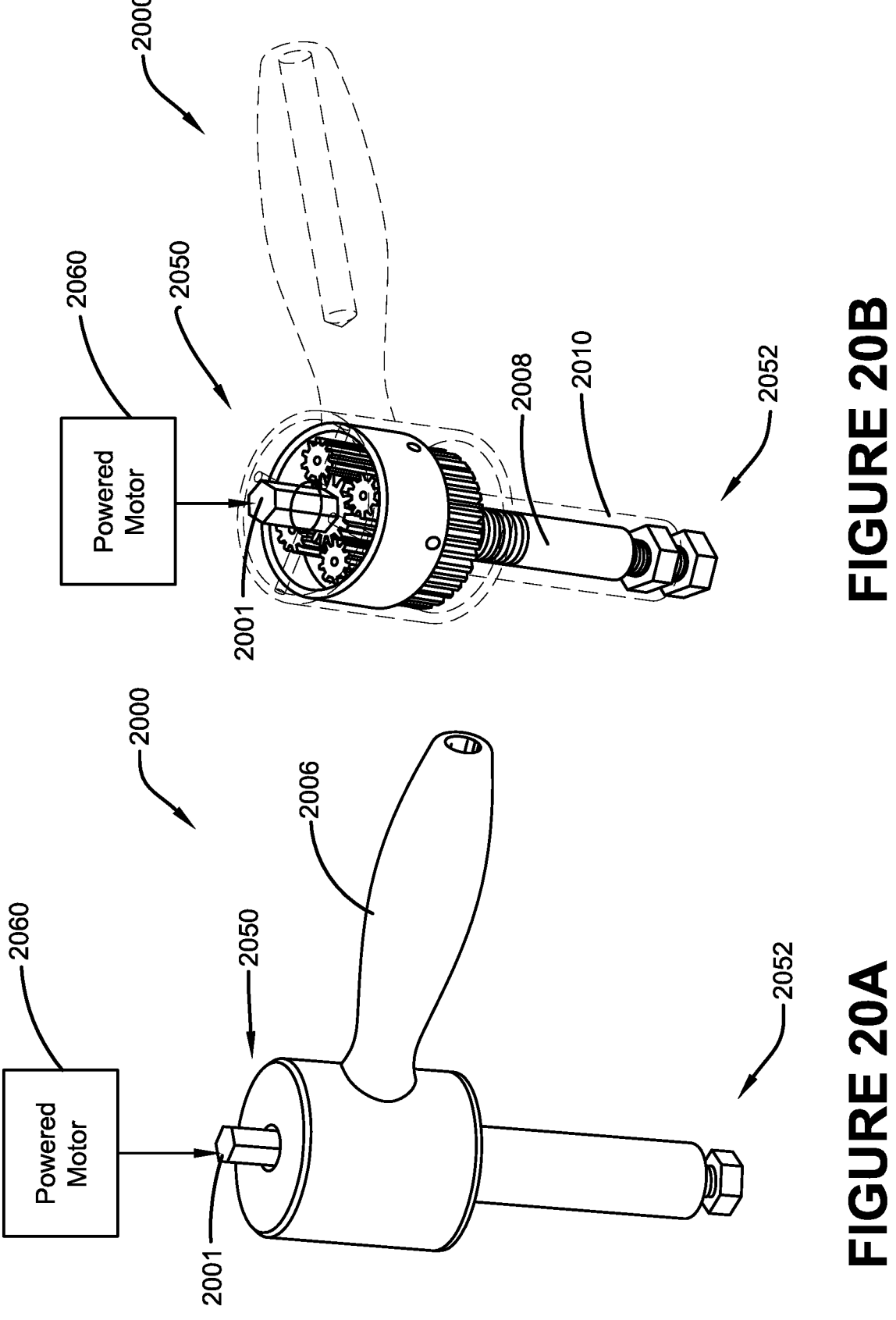
FIGS. 20A, 20B, and 20C are component diagram illustrating an example implementation of one or more portions of the one of more systems described herein, such as a driver adapted for non-manual power.
Figure 20C:
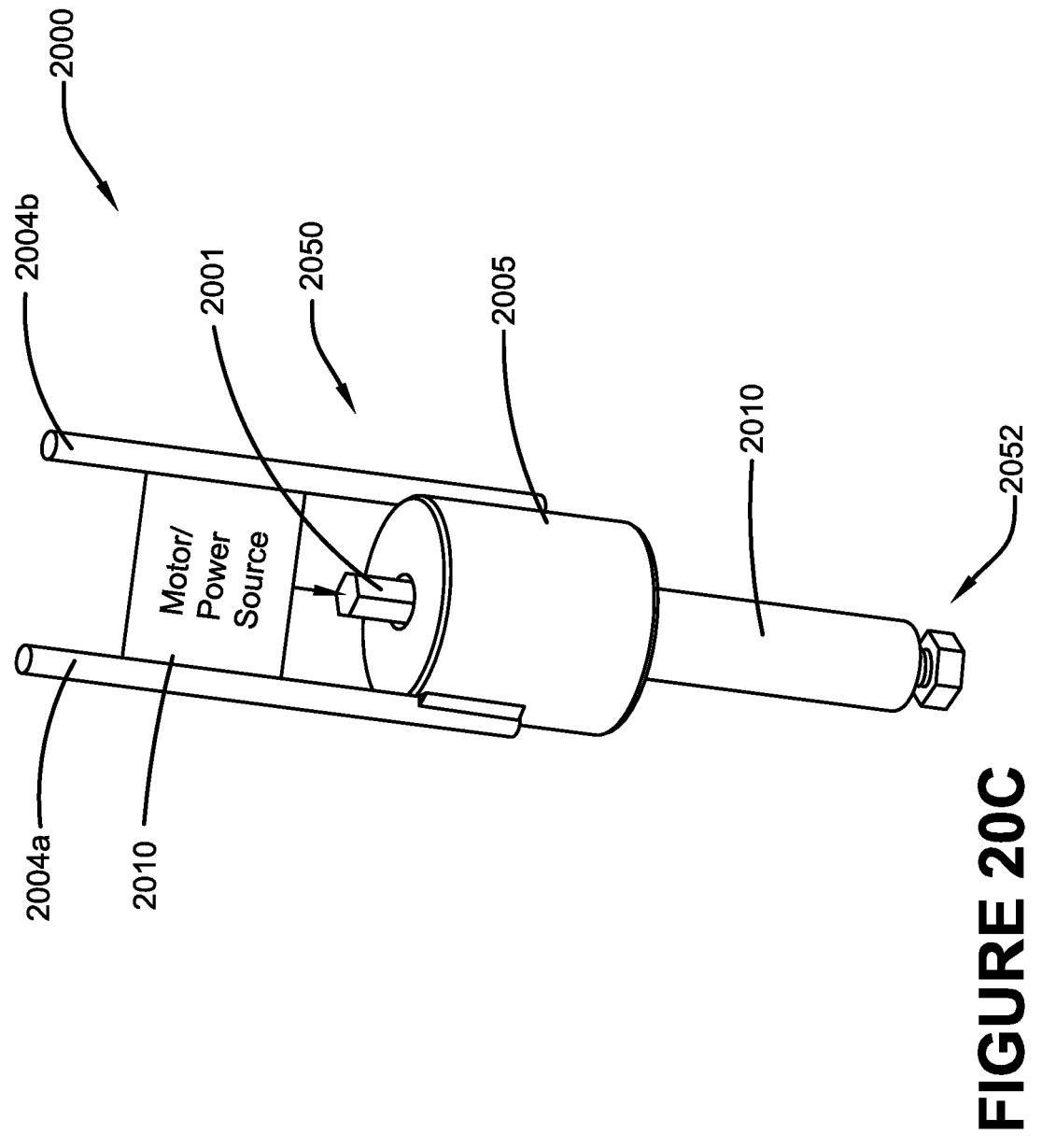

FIGS. 20A, 20B, and 20C are component diagrams that illustrate another alternate implementation of a device for applying torque and counter-torque. In this implementation, an example driver 2000 is adapted to receive a non-manual power source 2060 (e.g., a motor powered by a remote power source, such as a corded or cordless drill/driver). As illustrated in FIGS. 20A and 20B an example driver 2000 has a proximal or first end 2050 and a distal or second end 2052. On the proximal end 2050 there is a male hex shaft 2001. The male hex shaft 2001 can be fitted into a non-manual power source (such as a cordless drill, not shown). In this implementation, when torque is applied by a non-manual power source to the example driver 2000 through the male hex shaft 2001, a user can secure handle 2006 and apply counter torque by holding handle 2006 stationary. In the example shown, the driver 2000, optionally comprises a stationary inner shaft 2008 and an outer rotating tube 2010, this allows for example nut and bolt-type fastening at the distal end 2052 (described in detail below with FIG. 21).

In another implementation as illustrated in FIG. 20C, an example driver 2000 has a proximal or first end 2050 and a distal or second end 2052. On the proximal end 2050 there is a shaft adapter 2001 (e.g., male hex shaft, or other similar type of adapter) and posts 2004*a* and 2004*b*. The shaft adapter 2001 can be fitted into a non-manual power source 2010 (e.g., a cordless drill, portable motor, pneumatic power source, etc.). In some implementations, the power source 2010 can be disposed in the housing (e.g., 150 of FIG. 1) of the device 2000. In other implementations, the power source 2010 can be portable, and have a coupler (e.g., collar) configured to couple with the shaft adapter 2001, Further, in some implementations, the coupler may have holes configured, to receive posts 2004*a* and 2004*b*. The posts 2004*a* and 2004*b* are fixedly attached to the outer housing 2005, such that when torque is applied to the example driver 2000 through the male hex shaft 2001, the posts 2004*a* and 2004*b* received in the collar of the cordless drill apply counter torque. The example driver 2000, optionally comprises a stationary inner shaft 2008 (not shown) and an outer rotating tube 2010, this allows for example nut and bolt-type fastening at the distal end 2052 (described in detail below with FIG. 21).

Figures 21A, 21B:
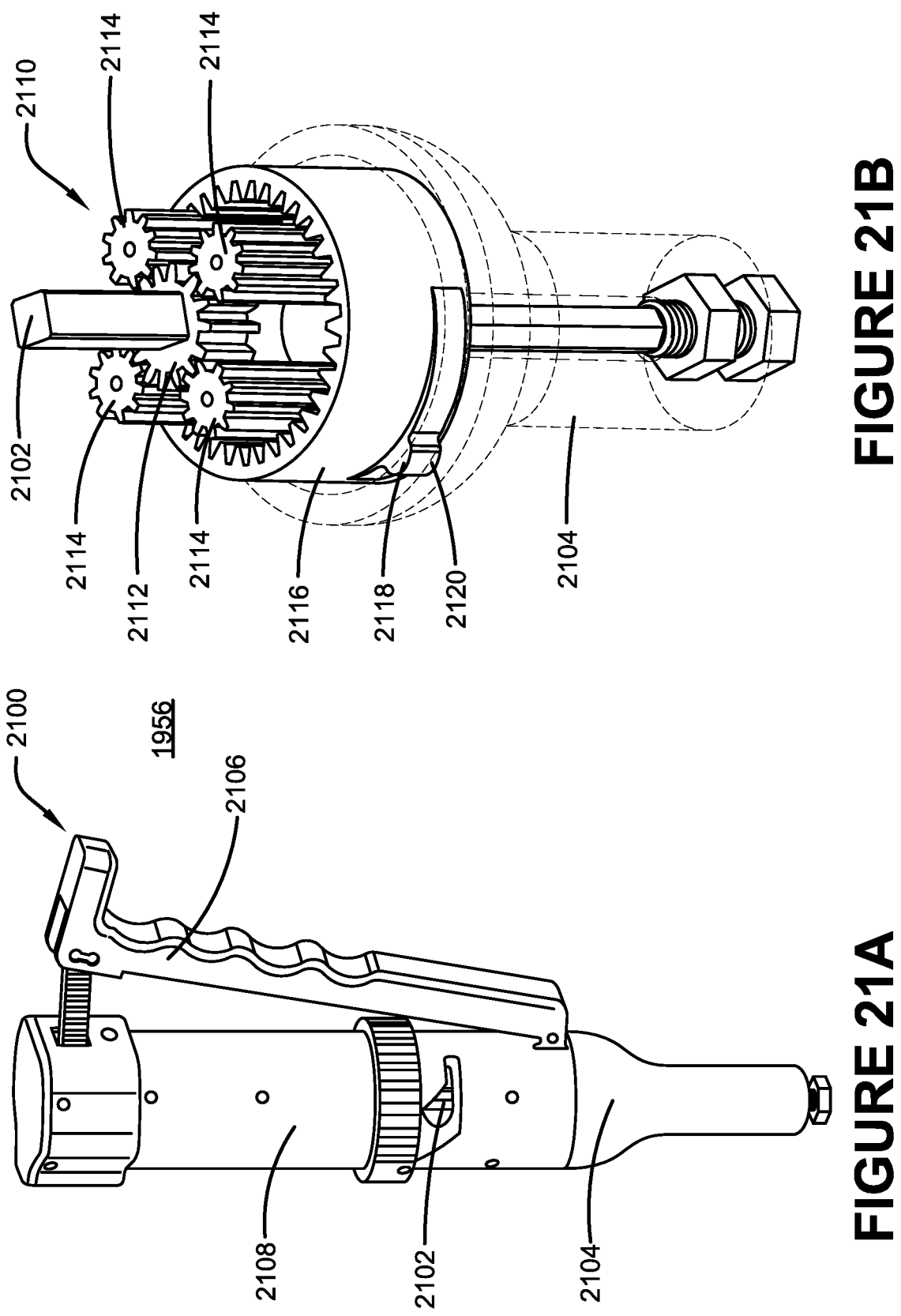
FIGS. 21A 21B, 21C, and 21D are component diagram illustrating an example implementation of one or more portions of the one of more systems described herein, such as a nut-bolt driver.

In FIGS. 21A, 21B, 21C, and 21D are component diagrams illustrating an example driver 2100 that contains a torque inversion mechanism 2110, which inverts or transmits the torque applied to the inner rotating input shaft 2102 to an outer rotating tube 2104. As shown in FIG. 21A, torque is manually applied through handle 2106 to an inner shaft 2102, the torque is transferred to the outer rotating tube 2104, such that outer rotating tube 2104 is the only rotating component, while the handle 2106 and housing 2108 are not rotating. As described in the implementations with FIGS. 19E, 19F, 19G, and 19H, the example driver 2100 may have an angled outer rotating tube 2104 to fasten a target in a tight or hard to reach situation. As described in the implementations with FIGS. 20A, 20B, and 20C, the example driver 2100 may be powered by a non-manual power source. In this implementation, the torque inversion mechanism 2110 can comprise a planetary gear arrangement. In some implementations, the planetary gear arrangement functions as the torque conversion mechanism (802 of FIGS. 8A-H) and the torque inversion mechanism 2110. FIG. 21B illustrates an implementation of the torque inversion mechanism 2110, comprising the input shaft 2102, a sun gear 2112, planetary gears 2114 (four planetary gears are shown, but any suitable number may be used), and an inverting ring gear 2116. In this implementation, the input shaft 2102 is fixedly attached to the sun gear 2112, the sun gear 2112 meshedly engages the planetary gears 2114, the planetary gears 2114 meshedly engage the inverting ring gear 2116, and the inverting ring gear 2116 is free to rotate. In this implementation, this results in planetary gears 2114 orbiting the sun gear 2114, providing rotation to the inverting ring gear 2116. In this implementation, a torque limiter such as described in FIGS. 17A, 17B, and 17C is used. The inverting ring gear 2116 has a pin 2118 that is operably connected into a notch 2120 of the outer rotating tube 2104, such that when the inverting ring gear 2116 rotates it causes the outer rotating tube 2104 to rotate. If the counter torque exceeds the torque capacity of the torque limiter, then the pin 2118 rotates out of the notch 2120 and the outer rotating tube 2104 cannot apply the tightening torque. Optionally, no torque limiter may be present to allow the inverting ring gear 2116 to be directly connected to the outer rotating tube 2104.

Figure 21D:
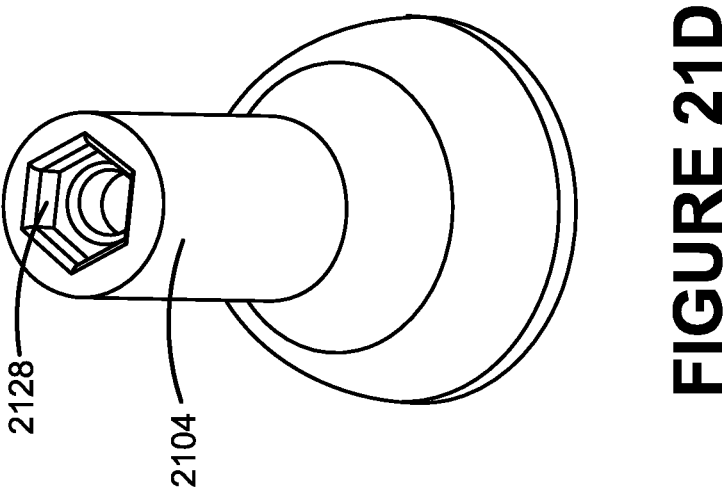
Figure 21C:
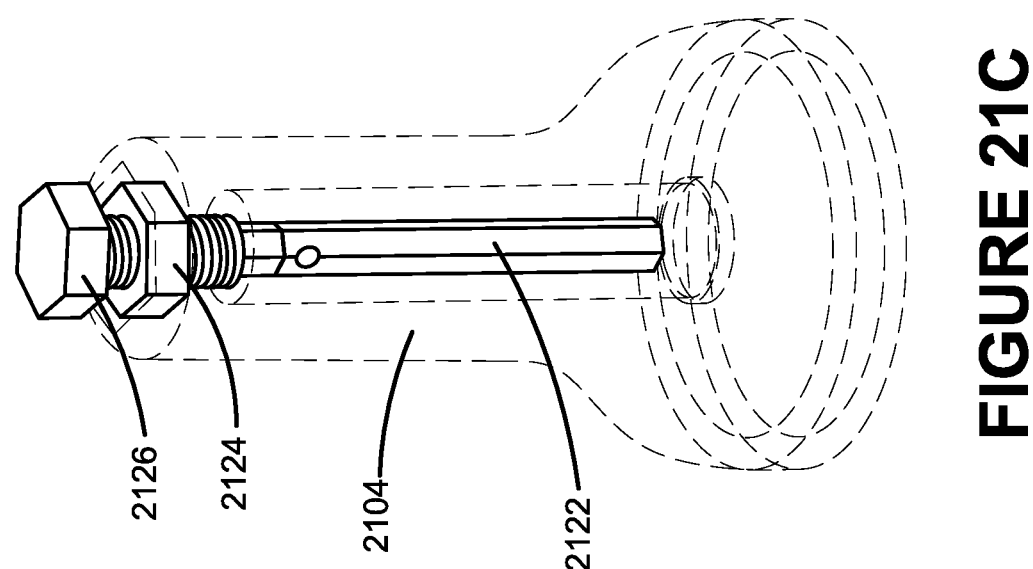

FIGS. 21C and 21D are bottom views of the example driver 2100. As shown in FIG. 21C, when the outer rotating tube 2104 is rotating, this allows for example nut and bolt-type fastening. In this implementation, a stationary inner shaft 2122 is disposed within the outer rotating tube 2104. The stationary inner shaft 2122 engages a bolt 2126 securing it with a male-female connection. As the stationary inner shaft 2122 secures the bolt 2126 and prevents it from rotating, the outer rotating tube 2104 rotates a nut 2124 threading it around the bolt 2126. As shown in FIG. 21D, the outer rotating tube 2104 has a hexagonal receiver 2128 to engage the nut 2124 (not shown) and cause it to rotate. The outer rotating tube 2104 sits on the nut 2126 during operation to apply torque. It may be appreciated, that the outer rotating tube 2104 may have a receiver-shape to engage any suitable fasteners.

Figures 22A, 22B:
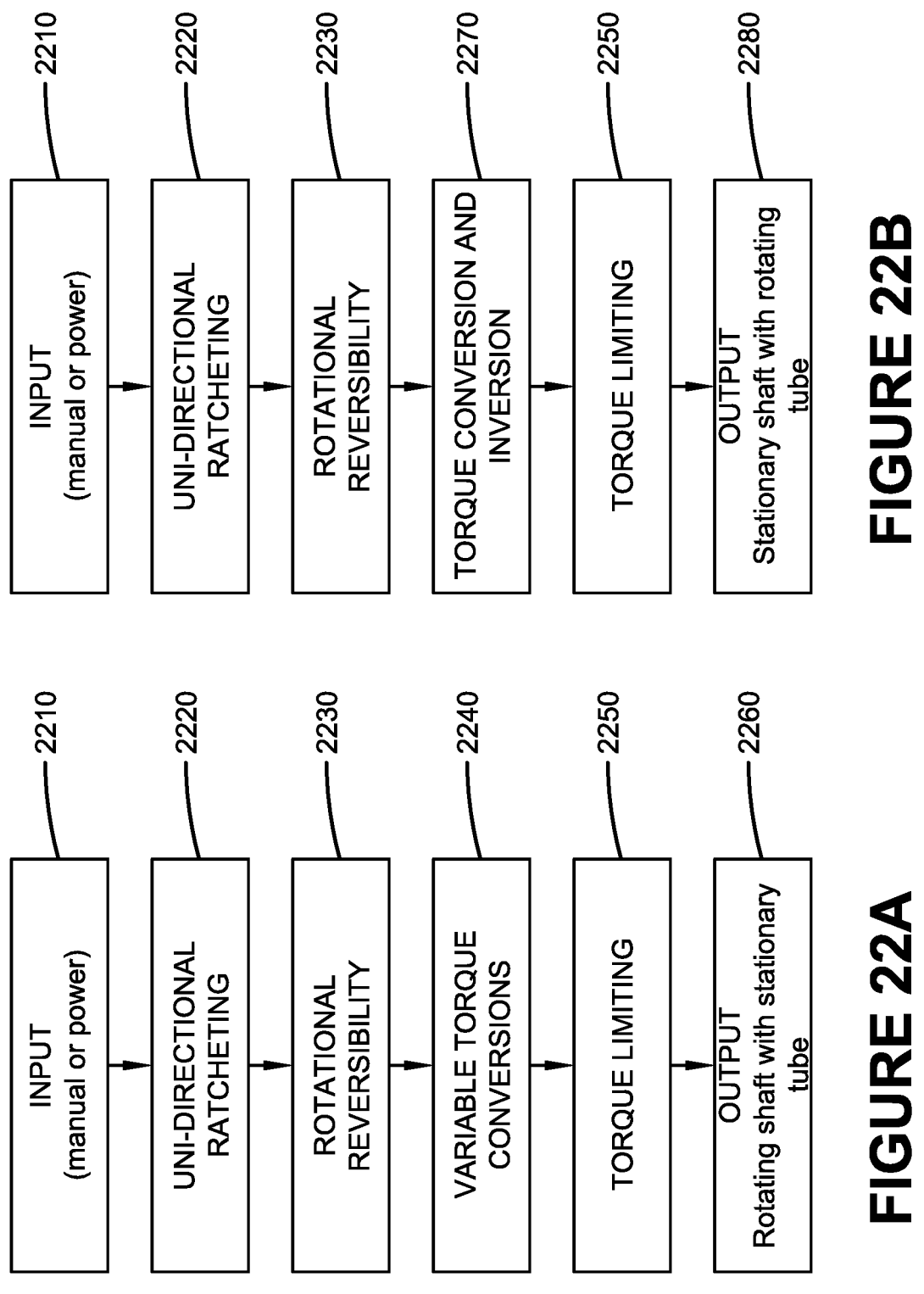
FIGS. 22A and 22B are flowcharts illustrating an example implementation of combinations of one or more portions of the one of more systems described herein.

In FIGS. 22A and 22B are flowcharts illustrating an example implementation of combinations of one or more portions of the one or more systems described herein. As shown in FIG. 22A, an input power source 2210 is applied to the input shaft of an example device. As described above (FIGS. 7A, 7B, 7C, and 10), as torque is applied from the input power source 2210 to the input shaft the uni-directionally ratcheting 2220 ensure uni-directional rotation, even if a reversal during, for example, manual operation occurs. As described above (FIGS. 4A, 4B, 11A, 11B, 11C, and 11D) the direction of torque applied to the input shaft may be reversed 2230 through a switch/button. As described above (FIGS. 8A, 8B, 8C, 8D, 8E, 8F, 8G, and 8H) the torque applied to the input shaft may be converted 2240 (such as 1:1, 1:2, 1:3, 1:4 etc.). As described above (FIGS. 9, 17A, 17B, 17C, 18A, 18B, 18C, 18D, 18E, 18F, and 18G), the torque applied to the input shaft may be limited 2250. As described above (FIGS. 6, 12, 13, 14, 15A, 15B, 16A, 16B, 19A, 19B, 19C, and 19D) the torque applied to the input shaft is transferred to the output, which is a rotating shaft, with a stationary tube/stationary housing 2260.

As shown in FIG. 22B, an input power source 2210 is applied to an input shaft of the example device. As described above (FIGS. 7A, 7B, 7C, and 10), as torque is applied from the input power source 2210 to the input shaft the uni-directionally ratcheting 2220 ensure uni-directional rotation, even if a reversal during, for example, manual operation occurs. As described above (FIGS. 4A, 4B, 11A, 11B, 11C, and 11D) the direction of torque applied to the input shaft may be reversed 2230 through a switch/button. As described above (FIGS. 8A, 8B, 8C, 8D, 8E, 8F, 8G, and 8H) the torque applied to the input shaft may be converted 2270 (such as 1:1, 1:2, 1:3, 1:4 etc.) and torque applied to input shaft is transferred/inverted 2270 to an outer tube. As described above (FIGS. 9, 17A, 17B, 17C, 18A, 18B, 18C, 18D, 18E, 18F, and 18G), the torque applied to the input shaft may be limited 2250). As described above (FIGS. 19E, 19F, 19G, 19H, 20A, 20B, 20C, 21A, 21B, 21C, and 21D) the torque applied to the input shaft is transferred to the rotating tube, with a stationary inner shaft 2280.

The word "exemplary" is used herein to mean serving as an example, instance or illustration. Any aspect or design described herein as "exemplary" is not necessarily to be construed as advantageous over other aspects or designs. Rather, use of the word exemplary is intended to present concepts in a concrete fashion. As used in this application, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Further, at least one of A and B and/or the like generally means A or B or both A and B. In addition, the articles "a" and "an" as used in this application and the appended claims may generally be construed to mean "one or more" unless specified otherwise or clear from context to be directed to a singular form.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated exemplary implementations of the disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes," "having," "has," "with," or variants thereof are used in either the detailed description or the claims, such terms are intended to be inclusive in a manner similar to the term "comprising."

The implementations have been described, hereinabove. It will be apparent to those skilled in the art that the above methods and apparatuses may incorporate changes and modifications without departing from the general scope of this invention. It is intended to include all such modifications and alterations in so far as they come within the scope of the appended claims or the equivalents thereof.

What is claimed is:

1. A device that applies torque to rotate a target tool engaging a complementary target component, and applies counter torque to stabilize the device with regard to a target base engaged with the target component, comprising;

a housing configured to be operably held by an operator with one hand, the housing having a housing axis that extends along the length and through the center of the housing;

an inner shaft configured to selectably rotate relative to the housing, the inner shaft having a first rotational axis that extends along the length of the shaft and is coaxial with the housing axis;

an outer tube configured to selectably rotate relative to the housing, the outer tube having a second rotational axis that extends along a length of the outer tube and is coaxial with the housing axis, the inner shaft being disposed within and coaxial with the second axis; and a torque inversion mechanism that is selectable to provide a first operation mode and a second operation mode, the torque inversion mechanism having an input shaft, wherein in the first operation mode the input shaft is operably coupled to the inner shaft to rotate the inner shaft and provide torque to the target tool and the outer tube is fixedly engaged with the target base to apply counter-torque to the target base, and in the second operation mode, the inner shaft is fixedly engaged with the target tool to apply counter-torque to the target tool and the input shaft is operably coupled to the outer tube rotates to rotate the outer tube and provide torque to the target base, wherein a power input operably provides power to the input shaft.

2. The device of claim 1, the inner shaft comprising a distal end that is configured to selectably engage with a first target tool complementary to a first target component, and a second, different target tool complementary to a second, different target component.

3. The device of claim 1, the power input comprising a manually operated actuator that provides power when actuated by an operator.

4. The device of claim 1, an actuator comprising a handle and an activator gear, wherein compression of the handle translates the activator gear to provide power.

5. The device of claim 4, comprising a power input drive engaged with the activator gear and disposed in the housing, and comprising one or more gears that convert a linear translation of the activator gear into rotational force.

6. The device of claim 1, comprising a ratcheting mechanism disposed in the housing, wherein the ratcheting mechanism allows for rotation of the inner shaft in a first direction, and mitigates rotation of the inner shaft in a second direction.

7. The device of claim 6, wherein the ratcheting mechanism is selectably reversible to mitigate rotation of the inner shaft in the first direction and allow rotation of the inner shaft in the second direction.

8. The device of claim 1, comprising a torque conversion mechanism, comprising gears that provide an increase in output torque relative to input torque.

9. The device of claim 8, wherein the torque conversion mechanism is selectably adjustable such that a ratio of output torque to input torque can be adjusted.

10. The device of claim 1, the power input comprising a motor that provides power supplied by separate power source for the rotating shaft.

11. The device of claim 1, comprising a power input coupler disposed at a proximal end of the housing, the power input coupler configured to operably engage with a portable power source to provide the power.

12. The device of claim 1, wherein the power input, the inner shaft, and the outer tube, combine with the housing such that the device is appropriately operated using a one-handed operation to selectably drive the target tool with respect to the target base.

13. The device of claim 1, the outer tube comprising a selectably replaceable engagement body that is selected to complement the target base, wherein a first engagement body is complementary to a first target base, and a second engagement body is complementary to a second target base.

14. The device of claim 1, comprising a rotary inversion mechanism that is selectable to provide for rotation of the inner shaft in a first direction and to provide for rotation of the inner shaft in a second direction.

15. The device of claim 1, comprising a torque limiter having an input sleeve operably and radially engaged with an output housing to rotate the output housing, the input sleeve being configured to disengage from the output housing to mitigate further transmission of torque at a selectably preset torque level.

16. The device of claim 1, wherein the inner shaft is selectably retractable into the housing.

17. An apparatus that applies torque to a target tool and counter torque to stabilize the apparatus with regard to a target base, comprising:

a selectably removable tip assembly comprising:

an inner shaft comprising a distal end, a target tool engaged with the distal end wherein the inner shaft operably rotates in order to rotate the target tool, and wherein the target tool is configured to engage a target component that is operably engaged with a target base;

an outer tube comprising a body that is shaped to selectably, fixedly engage with the target base the outer tube being coaxial with the rotating shaft; and a torque inversion mechanism that is selectable to provide a first operation mode and a second operation mode, the torque inversion mechanism having an input shaft, wherein in the first operation mode the input shaft is operably coupled to the inner shaft to rotate the inner shaft and provide torque to the target tool and the outer tube is fixedly engaged with the target base to apply counter-torque to the target base, and in the second operation mode, the inner shaft is fixedly engaged with the target tool to apply counter-torque to the target tool and the input shaft is operably coupled to the outer tube to rotate the outer tube and provide torque to the target base, wherein a power input operably provides power to the input shaft.

18. A hand-operated device that applies both torque and counter-torque, comprising:

a housing configured to be operably held by a hand of an operator, the housing comprising a proximal end and distal end;

an inner shaft disposed at the distal end of the housing, the shaft rotating relative to the housing to operably rotate a target tool selectably disposed at a distal end of the inner shaft, wherein the target tool is shaped to operably engage with a target component that is engaged with a target base;

an outer tube engaged with, and disposed at, the distal end of the housing, and comprising a body that is shaped to selectably, fixedly engage with the target base, the outer tube being coaxial with the inner shaft;

a torque limiter having an input sleeve operably and radially engaged with an output housing to rotate the output housing, the input sleeve being configured to disengage from the output housing to mitigate further transmission of torque at a selectably preset torque level; and a torque inversion mechanism that is selectable to provide a first operation mode and a second operation mode, the torque inversion mechanism having an input shaft, wherein in the first operation mode the input shaft is operably coupled to the inner shaft to rotate the inner shaft and provide torque to the target tool and the outer tube is fixedly engaged with the target base to apply counter-torque to the target base, and in the second operation mode, the inner shaft is fixedly engaged with the target tool to apply counter-torque to the target tool and the input shaft is operably coupled to the outer tube to rotate the outer tube and provide torque to the target base, wherein a power input disposed at the proximal end of the housing operably provides power to the input shaft.

* * * * *